United States Patent
Hashimoto et al.

(10) Patent No.: US 12,138,244 B2
(45) Date of Patent: Nov. 12, 2024

(54) DRUG AND METHOD OF TREATING OR PREVENTING RENAL DISEASE USING DRUG

(71) Applicants: Showa University, Tokyo (JP); Ji Xing Pharmaceutical Hong Kong Limited, Shanghai (CN)

(72) Inventors: Terumasa Hashimoto, Tokyo (JP); Keita Shibata, Tokyo (JP); Kazuo Honda, Tokyo (JP); Koji Nobe, Tokyo (JP)

(73) Assignees: SHOWA UNIVERSITY, Tokyo (JP); JI XING PAHRMACEUTICALS HONG KONG LIMITED, Shanghai (CN)

( * ) Notice: Subject to any disclaimer, the term of this patent is extended or adjusted under 35 U.S.C. 154(b) by 869 days.

(21) Appl. No.: 16/982,523

(22) PCT Filed: Feb. 26, 2019

(86) PCT No.: PCT/JP2019/007339
§ 371 (c)(1),
(2) Date: Sep. 18, 2020

(87) PCT Pub. No.: WO2019/181388
PCT Pub. Date: Sep. 26, 2019

(65) Prior Publication Data
US 2021/0000794 A1    Jan. 7, 2021

(30) Foreign Application Priority Data

Mar. 23, 2018  (JP) ................................ 2018-057055

(51) Int. Cl.
*A61K 31/407*    (2006.01)
*A61P 13/12*     (2006.01)

(52) U.S. Cl.
CPC ............ *A61K 31/407* (2013.01); *A61P 13/12* (2018.01)

(58) Field of Classification Search
CPC .............................. A61K 31/407; A61P 13/12
See application file for complete search history.

(56) References Cited

U.S. PATENT DOCUMENTS

| | | |
|---|---|---|
| 8,110,596 B2 | 2/2012 | Hasumi et al. |
| 8,193,173 B2 | 6/2012 | Hasumi et al. |
| 8,883,462 B2 | 11/2014 | Hasumi et al. |
| 9,078,880 B2 | 7/2015 | Honda et al. |
| 9,216,987 B2 | 12/2015 | Hasumi et al. |
| RE47,684 E | 11/2019 | Kazuo et al. |
| RE49,351 E | 1/2023 | Honda et al. |
| 2009/0216028 A1 | 8/2009 | Hasumi et al. |
| 2009/0270476 A1 | 10/2009 | Hasumi et al. |

FOREIGN PATENT DOCUMENTS

| | | |
|---|---|---|
| JP | 2004-224737 A | 8/2004 |
| JP | 2004-224738 A | 8/2004 |
| JP | 2008201688 A | 9/2008 |
| JP | 2011157293 A | 8/2011 |
| WO | 2007/111203 A1 | 4/2007 |
| WO | WO-2007094071 A1 | 8/2007 |
| WO | 2007/040082 A1 | 10/2007 |
| WO | WO-2012115209 A1 | 8/2012 |

OTHER PUBLICATIONS

Written Opinion issued in corresponding International Patent Application No. PCT/JP2019/007339 dated May 14, 2019.
European Search Report and Opinion issued in EP 19770431.5 dated Oct. 22, 2021.
International Search Report issued in corresponding International Patent Application No. PCT/JP2019/007339 dated May 14, 2019.
Takayasu et al., "Enhancement of fibrin binding and activation of plasminogen by staplabin through induction of a conformational change in plasminogen," FEBS Letter, 418: 58-62 (1997).
Matsumoto et al., Soluble Epoxide Hydrolase as an Anti-inflammatory Target of the Thrombolytic Stroke Drug SMTP-7, The Journal of Biological Chemistry, 289 (52): 35826-35838 (2014).
Kemmochi et al., "Protective Effect of Stachybotrys microspora Triprenyl Phenol-7 on the Deposition of IgA to the Glomerular Mesangium in Nivalenol-induced IgA Nephrpathy Using BALB/c Mice," Journal of Toxicologic Pathology, 25 (2): 149-154 (2012).
Shibata et al., "Evaluation of the effects of a new series of SMTPs in the acetic acid-induced embolic cerebral infarct mouse model," European Journal of Pharmacology, 818: 221-227 (2017).
Kodama et al., "Albumin fusion renders thioredoxin an effective anti-oxidative and anti-inflammatory agent for preventing cisplatin-induced nephrotoxicity," Biochimica et Biophysica Acta, 1840 (3): 1152-1162 (2014).
Tuzcu et al., "Protective Role of Zinc Picolinate on Cisplatin-Induced Nephrotoxicity in Rats," Journal of Renal Nutrition, 20 (6): 398-407 (2010).
Harada et al., "Diagnosis and Symptoms of Renal Failure," Journal of the Japanese Society of Internal Medicine, 87(7): 1234-1240 (1998) (see English abstract).
Chinese Office Action and Search Report issued in Application No. 201980020674.9 dated Dec. 7, 2022.

(Continued)

*Primary Examiner* — Bruck Kifle
(74) *Attorney, Agent, or Firm* — WILSON SONSINI GOODRICH & ROSATI

(57) ABSTRACT

A drug for renal disease, the drug including a compound represented by the following Formula (I) as an active ingredient.

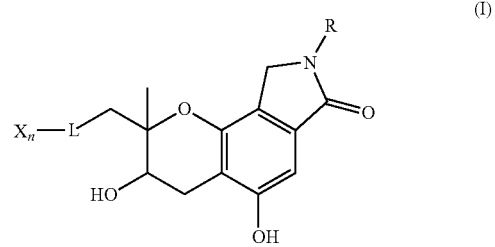

19 Claims, 3 Drawing Sheets

(56) References Cited

OTHER PUBLICATIONS

Oh et al., "Cisplatin-induces Kidney Dysfunction and Perspectives on Improving Treatment Strategies", Electrolyte Blood Press, 2014, vol. 12, pp. 55-65.

DRUG AND METHOD OF TREATING OR PREVENTING RENAL DISEASE USING DRUG

TECHNICAL FIELD

The present invention relates to a drug and a method of treating or preventing renal disease using the drug.

BACKGROUND ART

The kidney has important functions for organisms, such as maintenance of body fluid homeostasis through urine production, excretion of protein metabolites such as urea, and endocrine and metabolic regulation.

Renal disease is a general term for pathological conditions that causes a decrease in renal function in the kidney, and is broadly classified into acute renal disease and chronic renal disease. The progression of both the diseases leads to renal failure. Renal failure is a condition in which 70% or more of the renal function is lost. Further, 90% or more of the function is lost in end-stage renal failure with more advanced symptoms, which requires dialysis and transplantation. Acute renal disease includes acute renal failure and cisplatin nephropathy, and chronic renal disease includes chronic renal failure.

The description in the Journal of the Japanese Society of Internal Medicine, Vol. 87 (1998), No. 7, pp. 1234-1240 can be referred to for the staging of the symptoms of renal failure and the clinical symptoms.

*Stachybotrys microspora* triprenyl phenol (SMTP) compounds are a group of compounds having a triprenyl phenol skeleton produced by a filamentous bacterium, and are known to have a thrombolysis promotion action and a vascularization inhibitory action according to Japanese Patent Application Laid-Open (JP-A) No. 2004-224737, JP-A No. 2004-224738, and WO 2007/111203 A. With reference to the thrombolysis promotion action, an action mechanism is indicated by FEBS Letter 1997; 418:58-62, that an SMTP compound causes a change in the conformation of plasminogen, resulting in increasing the sensitivity of the plasminogen to t-PA and the binding of the plasminogen onto a thrombus or the like so as to promote lysis of the thrombus. Further, J Biol Chem 2014; 289:35826-35838 indicates that the SMTP compound has an excellent anti-inflammatory action.

Furthermore, WO 2007/040082 describes a composition for treating nephritis, which contains the SMTP compound as an active ingredient.

SUMMARY OF INVENTION

Technical Problem

The present inventors have found that a compound represented by Formula (I) has a therapeutic or preventive effect on renal disease.

Although the mechanism in which the compound exerts a therapeutic effect or a preventive effect on renal disease is not clarified, it is presumed as follows.

Although the details of the pathogenesis of renal disease are unknown, it has been suggested that oxidative stress and inflammation may be one of the causes. Since it has been confirmed that the compound described above has an anti-oxidant action, it is presumed that the action on renal disease is also based on a combination of anti-inflammatory action and antioxidative action.

In JP-A Nos. 2004-224737 and 2004-224738, WO 2007/111203, FEBS Letter 1997; 418:58-62, and J Biol Chem 2014; 289:35826-35838, there is neither description nor suggestion on the details of effects of the compound represented by Formula (I) on renal disease.

Further, in WO 2007/040082, there is a description that as a result of a fibrinolytic response promotion action of the compound represented by Formula (I), a process of decomposing an anti-renal basement membrane antibody itself or an immune complex of the host corresponding to anti-renal basement membrane antibody is promoted, or local tissue proteolysis is promoted, whereby nephritis is prevented or treated. However, in WO 2007/040082, there is neither description nor suggestion on the action on renal disease due to the combination of anti-inflammatory action and antioxidative action.

A problem to be solved by an embodiment according to the present disclosure is to provide a drug having an excellent therapeutic or preventive effect on renal disease, and a novel use of a compound represented by Formula (I) as a drug.

Further, a problem to be solved by another embodiment according to the disclosure is to provide a method of treating or preventing renal disease in a subject having or being at risk of developing renal disease, the method including administering a drug containing the compound represented by Formula (I) as an active ingredient to the subject.

Solution to Problem

Measures for solving the above problem include the following embodiments:

<1> A drug for renal disease, the drug including a compound represented by the following Formula (I) as an active ingredient.

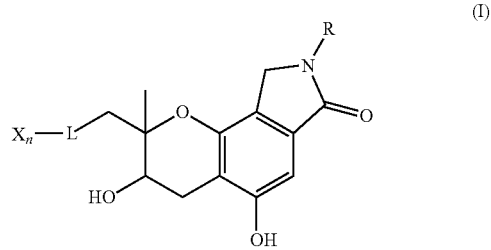

In Formula (I), L represents an aliphatic hydrocarbon group having a carbon number of from 4 to 10, X represents a hydroxy group or a carboxy group, n represents an integer from 0 to 2, and R represents a hydrogen atom or a substituent having a molecular weight of 1000 or less.

<2> The drug according to <1>, wherein the compound represented by Formula (I) is a compound represented by the following Formula (IA).

(IA)

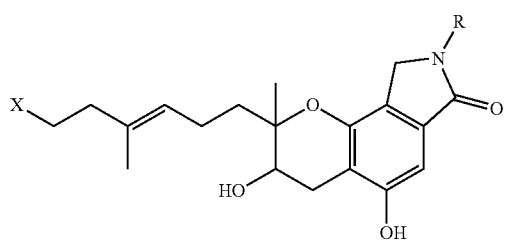

n represents an integer of 0 or 1, m represents an integer from 0 to 5, and * represents a bonding site:

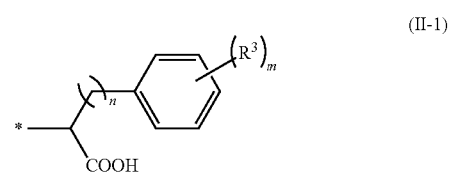
(II-1)

In Formula (IA), X is —CHY—C(CH$_3$)$_2$Z, each of Y and Z independently represents -H or —OH, or jointly form a single bond, and R represents a hydrogen atom or a substituent having a molecular weight of 1000 or less.

<3> The drug according to <1> or <2>, wherein the compound represented by Formula (I) is a compound represented by the following Formula (II) or (III).

(D) a substituent represented by -L$^1$-L$^2$-R$^4$, wherein L$^1$ represents a linking group including an alkylene group having a carbon number from 1 to 4 and having a carboxy group, L$^2$ represents a linking group expressed by —NH—C(=O)— or —NH—C(=S)—NH—, and R$^4$ represents a 9-fluorenylalkyloxy group having an alkyloxy group having a carbon number from 1 to 3, or (II)

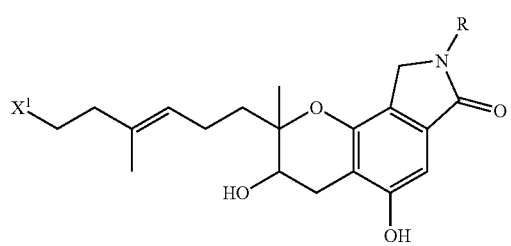

(III)

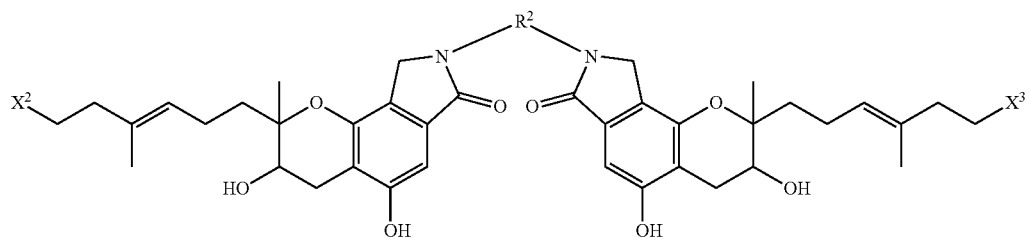

In Formula (II) and (III), each of X$^1$, X$^2$, and X$^3$ independently represents —CHY—C(CH$_3$)$_2$Z, each of Y and Z independently represents -H or —OH, or jointly form a single bond, and R$^1$ represents any one of the following (A) to (D):

(A) a residue of an amino compound, from which one amino group has been removed, selected from the group consisting of a natural amino acid, a D-isomer of a natural amino acid, and a compound derived by substituting at least one carboxy group in a natural amino acid or a D-isomer of a natural amino acid with a hydrogen atom, a hydroxy group, or a hydroxymethyl group, provided that —(CH$_2$)—OH is excluded;

(B) an aromatic group having at least one selected from the group consisting of a carboxy group, a hydroxyl group, a sulfonic acid group, and a secondary amino group as a substituent or a part of a substituent, or an aromatic group that contains a secondary amino group and may contain a nitrogen atom;

(C) an aromatic amino acid residue represented by the following Formula (II-1), wherein R$^3$ independently represents a substituent that may be present or absent and that represents a hydroxyl group, a carboxy group, or an alkyl group having a carbon number from 1 to 5, a polyheterocyclic group represented by the following Formula (II-2), wherein, in Formula (II-2), * represents a bonding site.

(II-2)

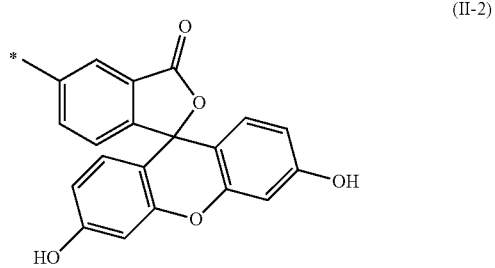

R$^2$ represents a residue of an amino compound, from which two amino groups have been removed, selected from the group consisting of a natural amino acid with two amino groups, a D-isomer of a natural amino acid with two amino groups, a compound derived by substituting at least one carboxy group in a natural amino acid with two amino groups, or a D-isomer of a natural amino acid with two amino groups, with a hydrogen atom, a hydroxy group, or a hydroxymethyl group, a compound represented by H₂N—CH(COOH)—(CH₂)$_n$—NH₂, wherein n is an integer from 0 to 9, and a compound represented by H₂N—CH(COOH)—(CH₂)$_m$—S$_p$—(CH₂)$_q$—CH(COOH)—NH₂, wherein each of m, p, and q independently represents an integer from 0 to 9.

<4> The drug according to any one of <1> to <3>, wherein the compound represented by Formula (I) includes at least one selected from the group consisting of the following SMTP-0, SMTP-1, SMTP-4, SMTP-5D, SMTP-6, SMTP-7, SMTP-8, SMTP-11 to 14, SMTP-18 to 29, SMTP-36, SMTP-37, SMTP-42, SMTP-43, SMTP-43D, SMTP-44, SMTP-44D, SMTP-46, and SMTP-47.

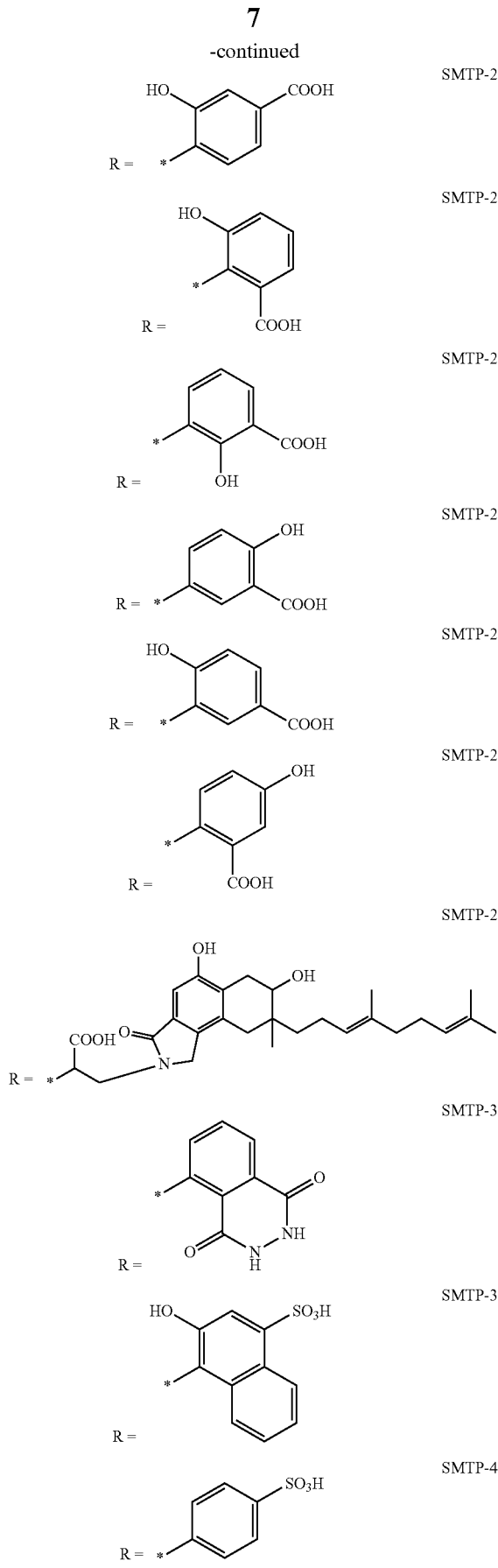
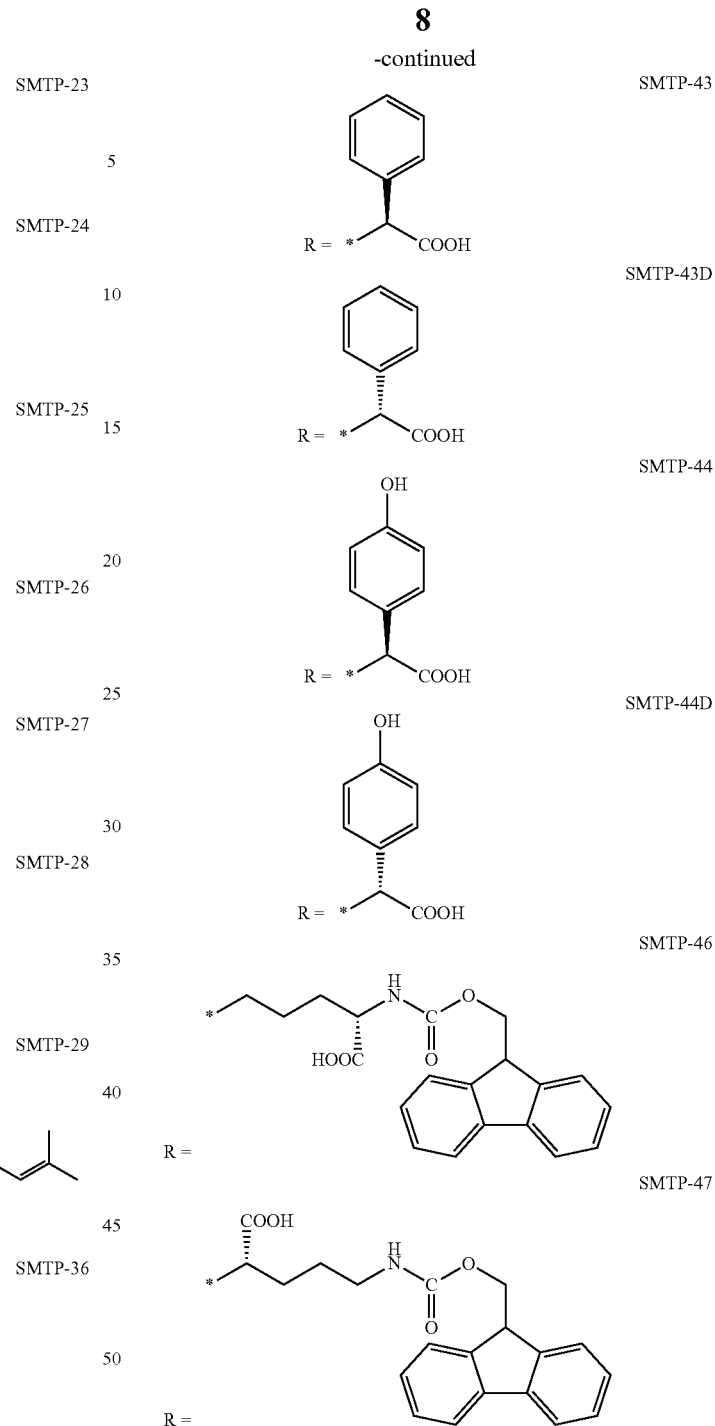

In the formula, * represents a bonding site.

<5> The drug according to <4>, wherein the compound represented by Formula (I) contains SMTP-7.

<6> The drug according to any one of <1> to <5>, wherein the renal disease is chronic renal disease.

<7> The drug according to any one of <1> to <5>, wherein the renal disease is acute renal disease.

<8> The drug according to <7>, wherein the acute renal disease is cisplatin nephropathy.

<9> A method of treating or preventing renal disease in a subject having or being at risk of developing renal disease, the method comprising administering the drug according to any one of <1> to <8> to the subject at an effective amount for treating or preventing renal disease.

<10> The drug according to any one of <1> to <8>, for treating or preventing renal disease.

<11> Use of a compound represented by Formula (I) for producing the drug according to any one of <1> to <8>, for treating or preventing renal disease.

<12> Use of a compound represented by the following Formula (I) in treating or preventing renal disease.

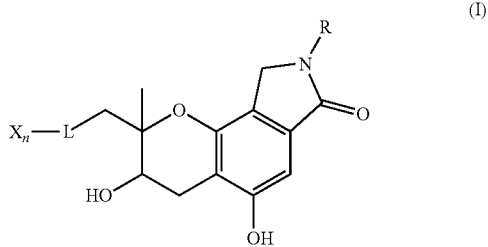

(I)

In Formula (I), L represents an aliphatic hydrocarbon group having a carbon number from 4 to 10, X represents a hydroxy group or a carboxy group, n represents an integer from 0 to 2, and R represents a hydrogen atom or a substituent having a molecular weight of 1000 or less.

Advantageous Effects of Invention

According to an embodiment of the disclosure, there can be provided a drug having an excellent therapeutic or preventive effect on renal disease and a novel use of the compound represented by Formula (I) as a drug.

Further, according to another embodiment of the disclosure, there can be provided a method of treating or preventing renal disease in a subject having or being at risk of developing renal disease, including administering a drug containing the compound represented by Formula (I) as an active ingredient to the subject.

DESCRIPTION OF EMBODIMENTS

Figure 1:
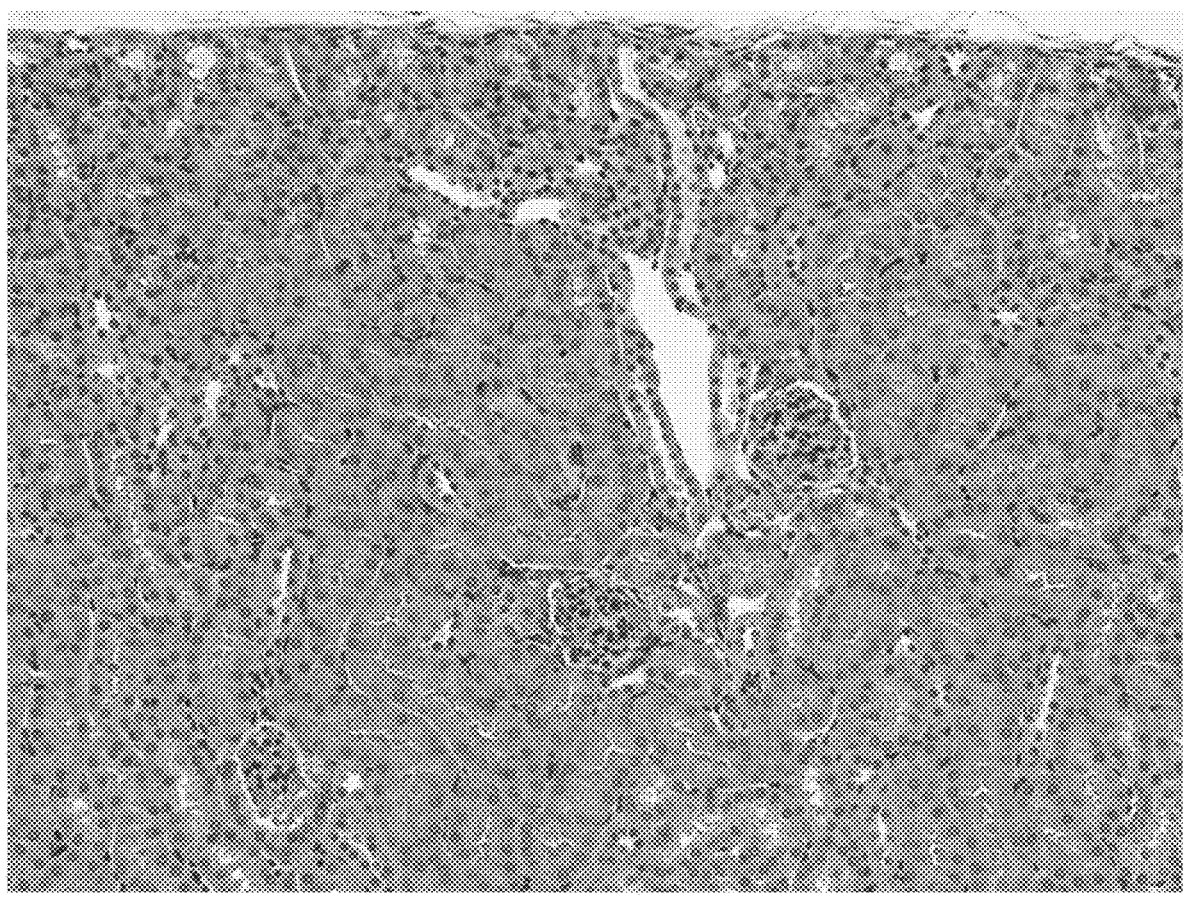
FIG. 1 is a view showing the result of HE staining in the Sham group in a test using an acute renal disease (cisplatin nephropathy) animal model.

The details of the disclosure will be described below. The explanation of the constituents described below may be made based on the representative embodiment of the disclosure, but the disclosure is not limited to such an embodiment.

In the numerical ranges described stepwise in the disclosure, an upper limit value or a lower limit value described in one numerical range may be replaced with another upper limit value or lower limit value described stepwise. An upper limit value or a lower limit value of the numerical ranges described in the disclosure may be replaced with a value shown in the examples.

In the disclosure, unless otherwise specified, the amount of each component in a composition such as a drug, in a case in which a plurality of substances corresponding to each component is present in the composition, indicates the total amount of the plurality of substances corresponding to each component in the composition.

In the specification, regarding the expression of a group (atomic group), in a case in which a group is not described to be "substituted" or "unsubstituted", the group refers not only to a group not having a substituent but also to a group having a substituent.

The term "step" in the specification refers not only to an independent step but also to a step that is not clearly distinguished from other steps as long as the intended purpose of the step is achieved.

In the disclosure, "% by mass" is the same as "% by weight", and "parts by mass" is the same as "parts by weight".

Further, in the disclosure, a combination of two or more preferred embodiments is a more preferred embodiment.

Hereinafter, the disclosure will be described in detail.

(Drug)

The drug according to the disclosure is a drug for renal disease, which contains a compound represented by Formula (I) as an active ingredient.

<Compound Represented by Formula (I)>

The drug according to the disclosure contains the compound represented by Formula (I).

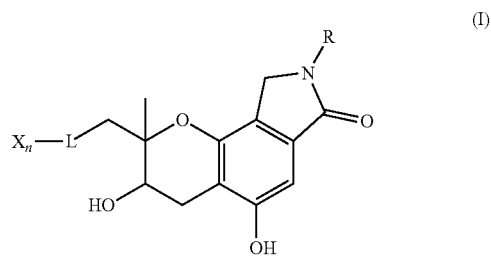

(I)

In Formula (I), L represents an aliphatic hydrocarbon group having a carbon number of from 4 to 10, X represents a hydroxy group or a carboxy group, n represents an integer from 0 to 2, and R represents a hydrogen atom or a substituent having a molecular weight of 1000 or less.

The aliphatic C4 to C10 hydrocarbon group represented by L may be linear, branched, or cyclic. Further, the aliphatic hydrocarbon group may also contain an unsaturated bond. Especially, an aliphatic hydrocarbon group which may have a linear or branched unsaturated bond is preferable.

In Formula (I), a group represented by $-L-X_n$ is preferably represented by any of the following Formula (V) and Chemical Formulae (Y1) to (Y4).

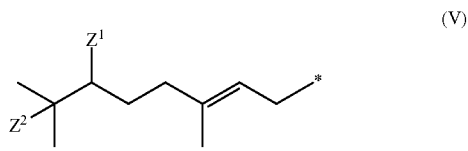

(V)

-continued

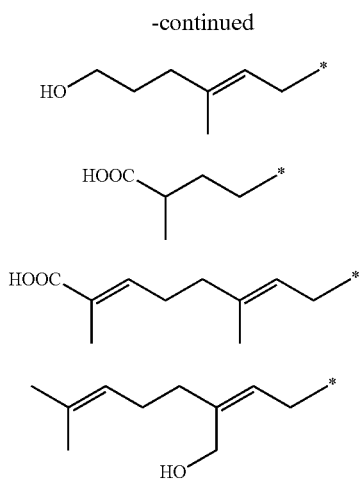

(Y1)
(Y2)
(Y3)
(Y4)

In Formula (V), each of $Z^1$ and $Z^2$ independently represents a hydrogen atom or a hydroxy group, or jointly form a single bond. Note that "*" in the chemical formulae represents a bonding position.

As the substituent having a molecular weight of 1,000 or less for R in Formula (I), from the viewpoint of suppressing renal insufficiency caused by ischemia described later, a substituent having a molecular weight of 800 or less is preferable, a substituent having a molecular weight of 700 or less is more preferable, and a substituent having a molecular weight of 600 or less is still more preferable.

Examples of R in Formula (I) include an α-amino acid. There is no particular restriction on an α-amino acid, and it may be a natural amino acid or a non-natural amino acid. Further, the α-amino acid may also be an amino acid derivative in which a substituent is introduced into a natural amino acid. Furthermore, in a case in which the α-amino acid has two or more amino groups, any amino group may be removed.

Especially, the α-amino acid is preferably a natural amino acid, a D-isomer of a natural amino acid, or phenylalanine or phenylglycine which may have at least one substituent selected from the group consisting of a hydroxy group, a carboxy group, and a C1 to C5 alkyl group, or is more preferably a natural amino acid, a D-isomer of a natural amino acid, or phenylglycine which may have at least one substituent selected from the group consisting of a hydroxy group, a carboxy group, and a C to C5 alkyl group.

There is no particular restriction on a natural amino acid insofar as it is an amino acid able to exist naturally. Examples thereof include glycine, alanine, threonine, valine, isoleucine, tyrosine, cysteine, cystine, methionine, histidine, aspartic acid, glutamic acid, asparagine, glutamine, arginine, lysine, hydroxylysine, ornithine, citrulline, homocysteine, 3,4-dihydroxyphenylalanine, homocystine, diaminopimelic acid, diaminopropionic acid, serine, leucine, phenylalanine, and tryptophan.

Examples of the substituent in an amino acid derivative in which a substituent is introduced into a natural amino acid include a nitro group, a hydroxy group, a C7 to C16 arylalkyl group, a ureido group, a thioureido group, a carboxy group, and a group formed by removing one hydrogen atom from fluorescamine. The substituent in the amino acid derivative may further have a substituent, if possible. The substituent which the substituent has is the same as the substituent in the amino acid derivative.

There is no particular restriction on an amino sugar for R in Formula (I) insofar as it is a sugar derivative having at least one amino group. Specific examples thereof include glucosamine, galactosamine, mannosamine, and neuraminic acid.

There is no particular restriction on a heterocyclic group for R in Formula (I) insofar as it is a cyclic group containing a hetero atom, and may be either an aliphatic heterocyclic group or an aromatic heterocyclic group. Further, examples of the hetero atom include a nitrogen atom, an oxygen atom, and a sulfur atom.

Especially, the heterocyclic group is preferably a nitrogen-containing heterocyclic group containing a nitrogen atom as a hetero atom, more preferably a heterocyclic group formed by removing one hydrogen atom from a heterocyclic compound selected from the group consisting of purine, pyridine, pyridazine, pyrrole, imidazole, pyrazole, and pyrazolone, and still more preferably a heterocyclic group formed by removing one hydrogen atom from a heterocyclic compound selected from the group consisting of purine, pyridine, and pyrazolone. Note that there is no particular restriction on a position for removing a hydrogen atom from the heterocyclic compound. Especially, it is preferable that the heterocyclic compound is removed from the carbon atom.

The heterocyclic group for R may have a substituent. Examples of the substituent in the heterocyclic group include a C1 to C5 alkyl group, a C14 or less aryl group, a carboxy group, a carbamoyl group, and a sulfonic acid group. Especially, the substituent is preferably at least one selected from a phenyl group or a carbamoyl group.

There is no particular restriction on the number of substituents in the heterocyclic group, but it is preferably 3 or less.

The C2 to C8 alkyl group for R in Formula (I) may be linear, branched, or cyclic. Especially, the alkyl group is preferably linear or branched, and more preferably linear. Further, the carbon number is preferably 2 to 6. Note that the carbon number of the alkyl group does not include the carbon number of the substituent on the alkyl group.

The alkyl group for R may have a substituent. Examples of the substituent in the alkyl group include a C1 to C5 alkyl group, a C14 or less aryl group, a C16 or less arylalkyl group, a hydroxy group, a carboxy group, a carbamoyl group, a sulfonic acid group, an amino group, a carbamoyloxy group, a ureido group, a thioureido group, an alkyl sulfide group, an alkyl disulfide group, a group formed by removing R from the compound represented by Formula (I), and a group formed by removing one hydrogen atom from fluorescamine. Especially, the substituent is preferably at least one selected from the group consisting of a hydroxy group, a carboxy group, an amino group, a carbamoyloxy group, a C7 to C14 arylalkyl group, a thioureido group, a group formed by removing R from the compound represented by Formula (I), and a group formed by removing one hydrogen atom from fluorescamine.

There is no particular restriction on the number of substituents in the alkyl group, but it is preferably 3 or less.

Further, the substituent in the alkyl group may additionally have a substituent, if possible. The substituent that the substituent has is the same substituent in the alkyl group.

The aryl group for R in Formula (I) is preferably a C6 to C14 aryl group, more preferably a C6 to C10 aryl group, and still more preferably a phenyl group.

The aryl group for R may have a substituent. Examples of the substituent in the aryl group include a C1 to C5 alkyl group, a C14 or less aryl group, a hydroxy group, a carboxy group, a sulfonic acid group, a carbamoyl group, and an arylcarbonyl group. Especially, the substituent is preferably at least one selected from the group consisting of a hydroxy group, a carboxy group, a sulfonic acid group, a carbamoyl group, and an arylcarbonyl group.

The number of substituents in the aryl group is not particularly limited, but is preferably 3 or less.

Further, the substituent in the aryl group may have a substituent, if possible. The substituent that the substituent has is the same as the substituent in the aryl group. Further, the substituents in the aryl group may be bonded to each other to form a cyclic structure, if possible.

[Method of Producing Compound Represented by Formula (I)]

The compound represented by Formula (I) used in the disclosure may be obtained by chemical synthesis, or may be obtained by purification of a culture of a filamentous bacterium, for example, *Stachybotrys microspora*. Examples of a method of obtaining the compound represented by Formula (I) by purification of a culture of a filamentous bacterium include a method including purification of an objective compound from a culture obtained by adding a predetermined additive organic amino compound to a culture liquid of *Stachybotrys microspora*. These methods are described in, for example, JP-A Nos. 2004-224737 and 2004-224738 and WO 2007/111203.

The compound represented by Formula (I) used in the disclosure may be an enantiomer, a diastereomer, and a mixture of enantiomers or a mixture of diastereomers. Such an enantiomer, a diastereomer, and a mixture of enantiomers or a mixture of diastereomers may be obtained by chemical synthesis, or may be obtained by purification of a culture of a filamentous bacterium. In the case of being obtained by purification of a culture of a filamentous bacterium, a D-isomer or an L-isomer of an additive organic amino compound to be added to a culture medium of a filamentous bacterium is used, so that the corresponding isomer can be obtained.

<Compound Represented by Formula (IA)>

The compound represented by Formula (I) is preferably a compound represented by the following Formula (IA).

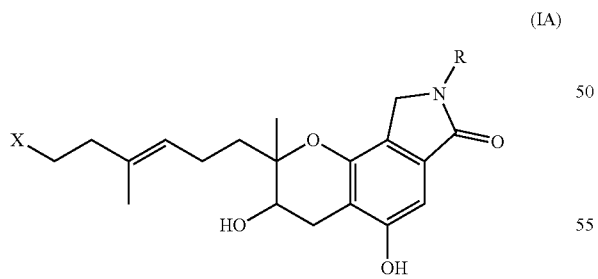

In Formula (IA), X is —CHY—C(CH$_3$)$_2$Z, each of Y and Z independently represents-H or —OH, or jointly form a single bond, and R represents a hydrogen atom or a substituent having a molecular weight of 1000 or less.

R in Formula (IA) is the same as R in Formula (I), and the preferred embodiments are also the same.

[Compound Represented by Formula (II)]

One of the specific examples of the compound represented by Formula (I) used in the disclosure is a compound represented by the following Formula (II).

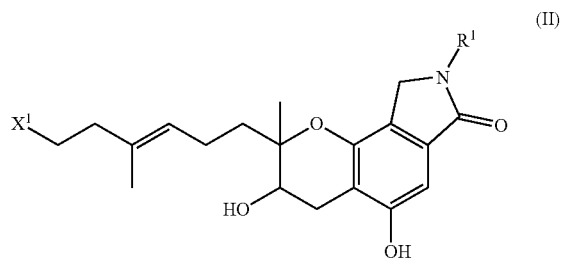

In Formula (II), X$^1$ represents —CHY—C(CH$_3$)$_2$Z, each of Y and Z independently represents —H or —OH, or jointly form a single bond, and R$^1$ represents any one of the following (A) to (D):

(A) a residue of an amino compound, from which one amino group has been removed, selected from the group consisting of a natural amino acid, a D-isomer of a natural amino acid, and a compound derived by substituting at least one carboxy group in a natural amino acid or a D-isomer of a natural amino acid with a hydrogen atom, a hydroxy group, or a hydroxymethyl group, provided that —(CH)$_2$—OH is excluded;

(B) an aromatic group having at least one selected from the group consisting of a carboxy group, a hydroxyl group, a sulfonic acid group, and a secondary amino group as a substituent or a part of a substituent, or an aromatic group that contains a secondary amino group and may contain a nitrogen atom;

(C) an aromatic amino acid residue represented by the following Formula (II-1), wherein R$^3$ independently represents a substituent that may be present or absent and that represents a hydroxyl group, a carboxy group, or an alkyl group having a carbon number from 1 to 5, n represents an integer of 0 or 1, m represents an integer from 0 to 5, and * represents a bonding site:

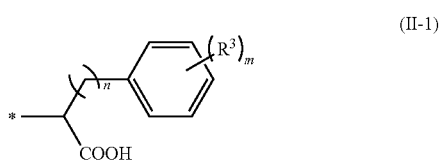

(D) a substituent represented by -L$^1$-L$^2$-R$^4$, wherein L$^1$ represents a linking group including an alkylene group having a carbon number from 1 to 4 and having a carboxy group, L$^2$ represents a linking group expressed by —NH—C(=O)— or —NH—C(=S)—NH—, and R$^4$ represents a 9-fluorenylalkyloxy group having an alkyloxy group having a carbon number from 1 to 3, or a polyheterocyclic group represented by the following Formula (II-2), wherein, in Formula (II-2), * represents a bonding site.

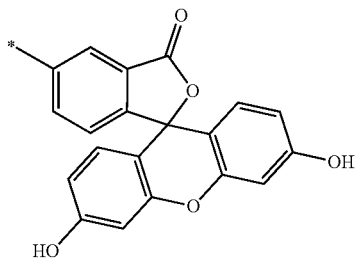

(II-2)

A compound according to Formula (II), in which $R^1$ is the (A), will be described.

The (A) is a residue of an amino compound, from which one amino group has been removed, selected from the group consisting of a natural amino acid, a D-isomer of a natural amino acid, and a compound derived by substituting at least one carboxy group in a natural amino acid or a D-isomer of a natural amino acid with a hydrogen atom, a hydroxy group, or a hydroxymethyl group, provided that $-(CH)_2-OH$ is excluded.

There is no particular restriction on a natural amino acid insofar as it is an amino acid able to exist naturally, and examples thereof include an α-amino acid, a β-amino acid, a γ-amino acid, and a δ-amino acid. Such an amino acid may be obtained from a natural product, or artificially by a method such as organic synthesis.

Examples of a natural amino acid include, as an α-amino acid, glycine, alanine, threonine, valine, isoleucine, tyrosine, cysteine, cystine, methionine, histidine, aspartic acid, glutamic acid, asparagine, glutamine, arginine, lysine, hydroxylysine, ornithine, citrulline, homocysteine, 3,4-dihydroxyphenylalanine, homocystine, diaminopimelic acid, diaminopropionic acid, serine, leucine, phenylalanine, and tryptophan; as a β-amino acid, β-alanine; as a γ-amino acid, γ-aminobutyric acid and carnitine; as a δ-amino acid, δ-aminolevulinic acid and 5-aminovaleric acid.

Examples of a compound derived by substituting at least one carboxy group in the natural amino acid and a D-isomer of the natural amino acid, with a hydrogen atom, a hydroxy group, or a hydroxymethyl group include an amino alcohol and an amine. Examples of the amino alcohol include 2-aminoethanol.

Specific examples of a compound according to Formula (II), in which $R^1$ is the (A), include the following compounds shown in Table 1. "Additive organic amino compound" in Table means an additive organic amino compound used when the compound is obtained by purification of a culture obtained by adding a predetermined additive organic amino compound to a culture liquid of *Stachybotrys microspora* (the same applies hereafter). In Table, * represents a bonding site (the same applies hereafter).

TABLE 1

SMTPs

| Compound No. | Molecular weight | R = | Additive organic amino compound |
|---|---|---|---|
| SMTP-3 | 473.6 |  | L-serine |
| SMTP-4 | 533.7 |  | L-phenylalanine |
| SMTP-4Me | 547.7 |  | L-phenylalanine methyl ester |
| SMTP-4D | 533.7 |  | D-phenylalanine |
| SMTP-5 | 499.6 |  | L-leucine |
| SMTP-5D | 499.6 |  | D-leucine |
| SMTP-6 | 572.7 |  | L-tryptophan |

TABLE 1-continued

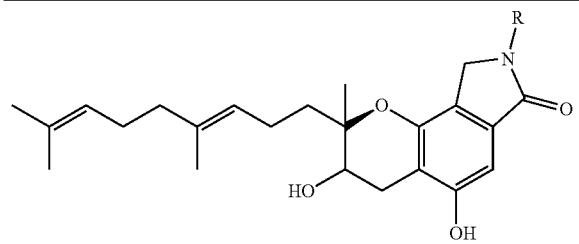

SMTPs

| Compound No. | Molecular weight | R = | Additive organic amino compound |
|---|---|---|---|
| SMTP-6D | 572.7 | 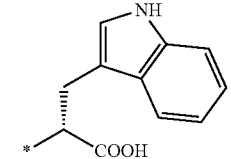 [SMILES: *[C@H](Cc1c[nH]c2ccccc12)C(=O)O] | D-tryptophan |
| SMTP-10 | 499.6 |  | L-isoleucine |
| SMTP-11 | 485.6 | 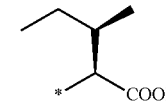 | L-valine |
| SMTP-12 | 457.6 |  | L-glycine |
| SMTP-13 | 517.7 | 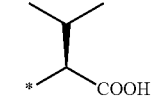 [SMILES: *[C@H](C(=O)O)C(C)C] | L-methionine |
| SMTP-14 | 549.7 |  | L-tyrosine |
| SMTP-15 | 542.7 | 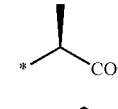 | L-arginine |

The compounds shown in Table 1 can be preferably used as the compound represented by Formula (I) used in the disclosure.

A compound according to Formula (II), in which $R^1$ is the (B), will be described.

The (B) is an aromatic group having at least one selected from the group consisting of a carboxy group, a hydroxyl group, a sulfonic acid group, and a secondary amino group as a substituent or a part of a substituent, or an aromatic group that contains a secondary amino group and may contain a nitrogen atom.

Examples of the aromatic group include groups represented by the following structural formulae. In each of the structural formulae, * represents a bonding site.

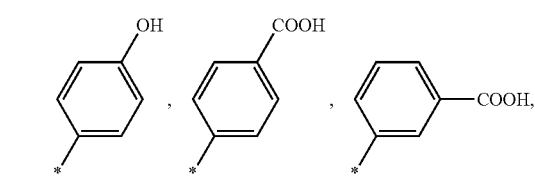

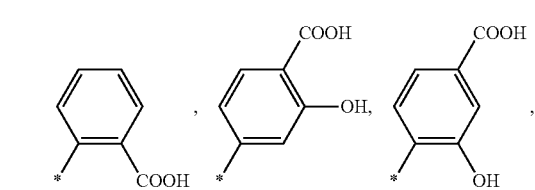

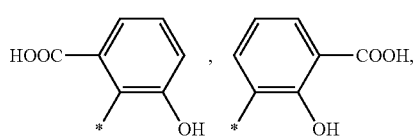

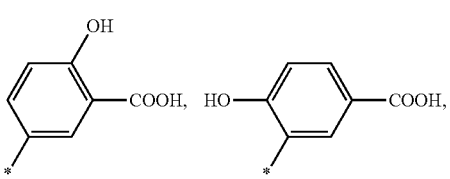

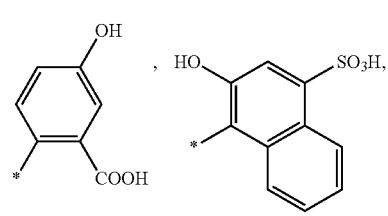

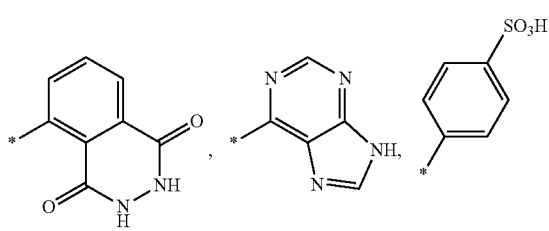

Specific examples of a compound according to Formula (II), in which $R^1$ is the (B), include the following compounds shown in Table 2.

TABLE 2

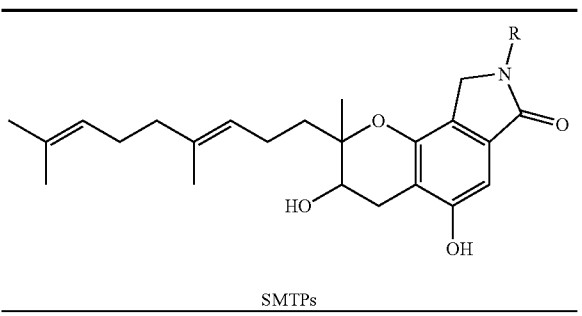

SMTPs

| SMTPs | | R = |
|---|---|---|
| SMTP-18 | 477.6 | 4-hydroxyphenyl |
| SMTP-19 | 505.6 | 4-carboxyphenyl |
| SMTP-20 | 505.6 | 3-carboxyphenyl |
| SMTP-21 | 505.6 | 2-carboxyphenyl |
| SMTP-22 | 521.6 | 2-hydroxy-4-carboxyphenyl |
| SMTP-23 | 521.6 | 3-hydroxy-4-carboxyphenyl |
| SMTP-24 | 521.6 | 2-hydroxy-5-carboxyphenyl |
| SMTP-25 | 521.6 | 2-hydroxy-3-carboxyphenyl |
| SMTP-26 | 521.6 | 2-hydroxy-5-carboxyphenyl |

TABLE 2-continued

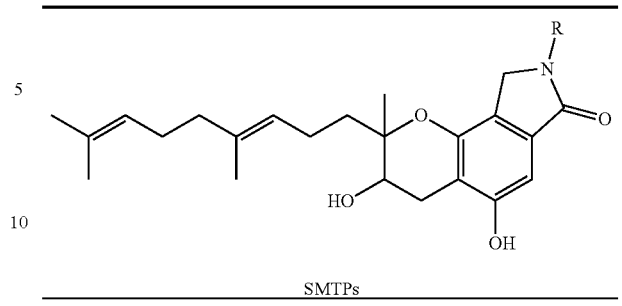

SMTPs

| SMTPs | | R = |
|---|---|---|
| SMTP-27 | 521.6 | 4-hydroxy-3-carboxyphenyl |
| SMTP-28 | 521.6 | 5-hydroxy-3-carboxyphenyl |
| SMTP-32 | 503.6 | purine |
| SMTP-36 | 545.3 | phthalazinedione |
| SMTP-37 | 607.7 | hydroxy-naphthyl-sulfonic acid |
| SMTP-42 | 541.7 | 4-sulfophenyl |

The compounds shown in Table 2 can be preferably used as the compound represented by Formula (I) used in the disclosure.

A compound according to Formula (II), in which $R^1$ is the (C), will be described.

The (C) is an aromatic amino acid residue represented by the following Formula (II-1), wherein $R^3$ is a substituent that may be present or absent and that represents at least one substituent selected from the group consisting of a hydroxyl group, a carboxy group, and an alkyl group having a carbon number from 1 to 5, n represents an integer of 0 or 1, m represents an integer from 0 to 5, and * represents a bonding site. The alkyl group may further have a substituent, and examples of the substituent include a hydroxyl group, an alkenyl group, an amino group, a carboxyl group, and a sulfhydryl group.

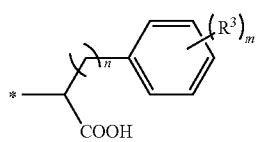

Examples of the aromatic amino acid residue represented by Formula (II-1) include groups represented by the following structural formulae. * represents a bonding site.

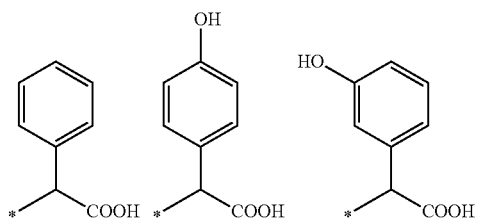

Specific examples of a compound according to Formula (II), in which $R^1$ is the (C), include the following compounds shown in Table 3.

TABLE 3

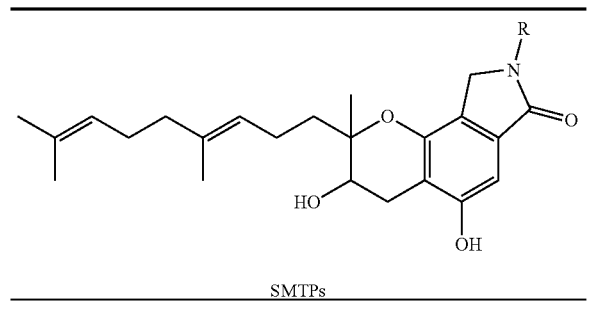

SMTPs

| | R = | |
|---|---|---|
| SMTP-43 | 519.6 | 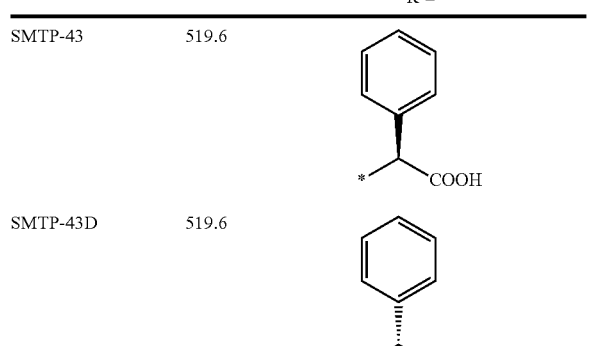 |
| SMTP-43D | 519.6 | |
| SMTP-44 | 535.6 | 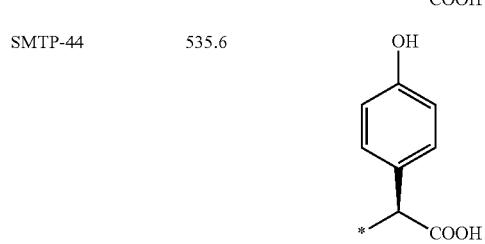 |

TABLE 3-continued

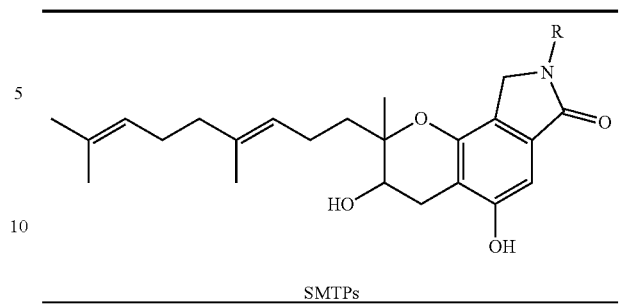

SMTPs

| | R = | |
|---|---|---|
| SMTP-44D | 535.6 | 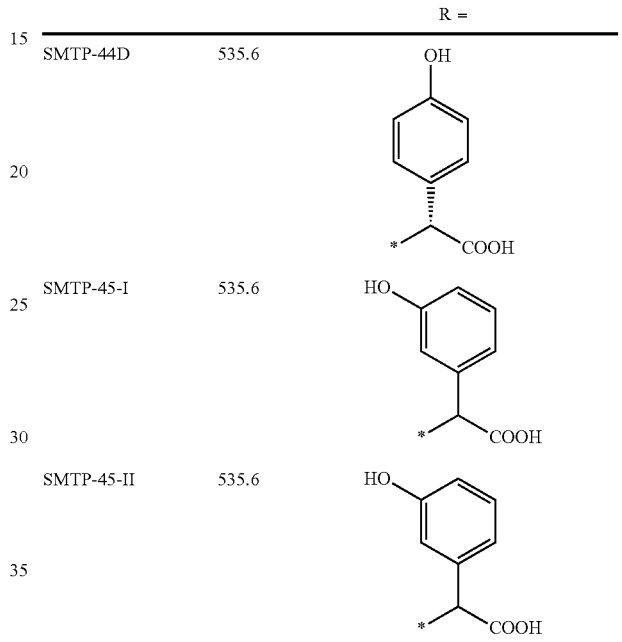 |
| SMTP-45-I | 535.6 | |
| SMTP-45-II | 535.6 | |

The compounds shown in Table 3 can be preferably used as the compound represented by Formula (I) used in the disclosure.

A compound according to Formula (II), in which $R^1$ is the (D), will be described.

The (D) is a substituent represented by $-L^1-L^2-R^4$, wherein $L^1$ represents a linking group including an alkylene group having a carbon number from 1 to 4 and having a carboxy group, $L^2$ represents a linking group expressed by —NH—C(=O)— or —NH—C(=S)—NH—, and $R^4$ represents a 9-fluorenylalkyloxy group having an alkyloxy group having a carbon number from 1 to 3, or a polyheterocyclic group represented by the following Formula (II-2).

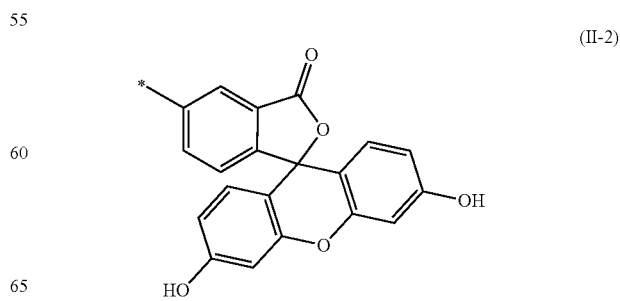

Specific examples of a compound according to Formula (II), in which $R^1$ is the (D), include the following compounds shown in Table 4.
TABLE 4
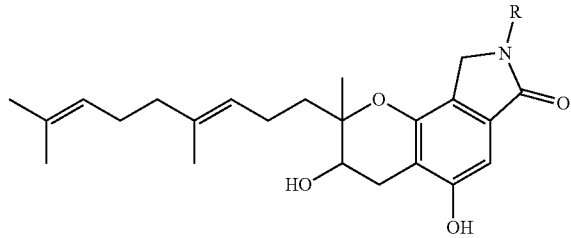
SMTPs
| | | R = |
|---|---|---|
| SMTP-46 | 722.9 | 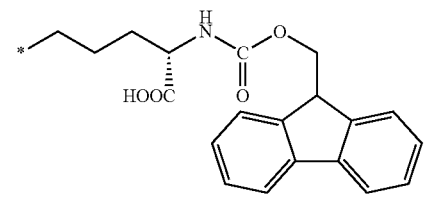 [SMILES: *CCC[C@H](NC(=O)OCC1c2ccccc2-c2ccccc21)C(=O)O] |
| SMTP-47 | 722.9 | 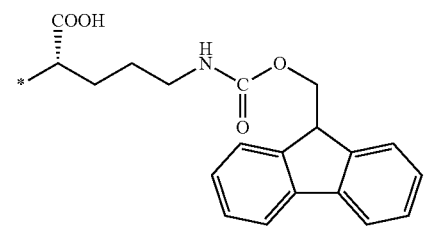 [SMILES: *[C@@H](CCCNC(=O)OCC1c2ccccc2-c2ccccc21)C(=O)O] |
| SMTP-48 | 890.0 | 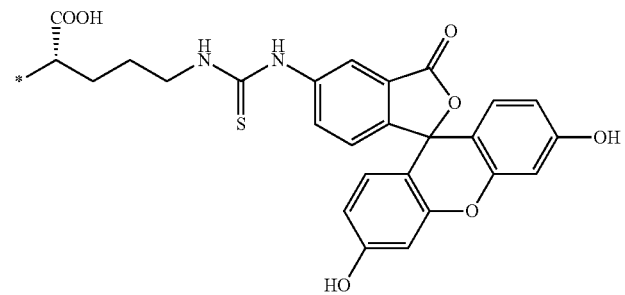 [SMILES: *[C@@H](CCCNC(=S)Nc1ccc2c(c1)C(=O)OC21c2ccc(O)cc2Oc2cc(O)ccc21)C(=O)O] |
| SMTP-49 | 890.0 | 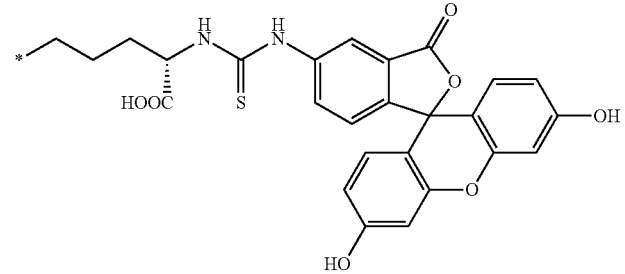 [SMILES: *CCC[C@H](NC(=S)Nc1ccc2c(c1)C(=O)OC21c2ccc(O)cc2Oc2cc(O)ccc21)C(=O)O] |
The compounds shown in Table 4 can be preferably used as the compound represented by Formula (I) used in the disclosure.

[Compound Represented by Formula (III)]

One of the specific examples of the compound represented by Formula (I) used in the disclosure is a compound represented by the following Formula (III).

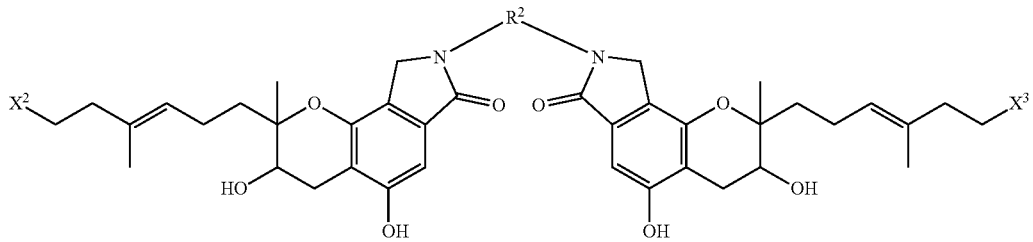

In Formula (III), each of $X^2$, and $X^3$ independently represents —CHY—C(CH$_3$)$_2$Z, each of Y and Z independently represents-H or —OH, or jointly form a single bond. $R^2$ represents a residue of an amino compound, from which two amino groups have been removed, selected from the group consisting of a natural amino acid with two amino groups, a D-isomer of a natural amino acid with two amino groups, a compound derived by substituting at least one carboxy group in a natural amino acid with two amino groups, or a D-isomer of a natural amino acid with two amino groups, with a hydrogen atom, a hydroxy group, or a hydroxymethyl group, a compound represented by H$_2$N—CH(COOH)—(CH$_2$)$_n$—NH$_2$, wherein n is an integer from 0 to 9, and a compound represented by H$_2$N—CH(COOH)—(CH$_2$)$_m$—S$_p$—(CH$_2$)$_q$—CH(COOH)—NH$_2$, wherein each of m, p, and q independently represents an integer from 0 to 9.

n represents an integer from 0 to 9, preferably an integer from 0 to 6, more preferably an integer from 1 to 5, and still more preferably an integer from 1 to 4.

m represents an integer from 0 to 9, preferably an integer from 0 to 4, more preferably an integer from 1 to 3, and still more preferably 1 or 2.

p represents an integer from 0 to 9, preferably an integer from 0 to 4, more preferably an integer from 1 to 3, and still more preferably 1 or 2.

q is an integer from 0 to 9, preferably an integer from 0 to 4, more preferably an integer from 1 to 3, and still more preferably 1 or 2.

When p is 0, m+q is preferably an integer from 0 to 9, more preferably an integer from 0 to 6, still more preferably an integer from 1 to 5, and particularly preferably an integer from 1 to 4.

Examples of a natural amino acid with two amino groups include, as an α-amino acid, hydroxylysine, citrulline, cystine, homocystine, diaminopimelic acid, diaminopropionic acid, lysine, and ornithine.

Examples of a compound derived by substituting at least one carboxy group in a natural amino acid with two amino groups, or a D-isomer of a natural amino acid with two amino groups, with a hydrogen atom, a hydroxy group, or a hydroxymethyl group include H$_2$N—(CH$_2$)$_k$—NH$_2$, wherein k is an integer from 1 to 10, preferably an integer from 1 to 6, and more preferably an integer from 1 to 4.

Specific examples of the compound represented by Formula (III) include the following compounds shown in Table 5.

TABLE 5

| | Molecular weight | R = | Additive organic amino compound |
|---|---|---|---|
| SMTP-7 | 869.1 | 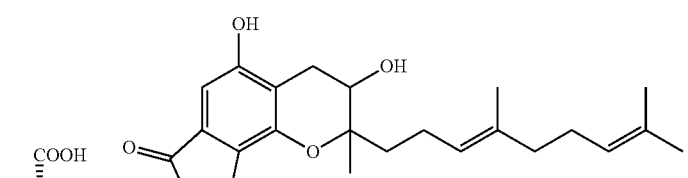 | L-ornitihine |
| SMTP-7D | 869.1 | 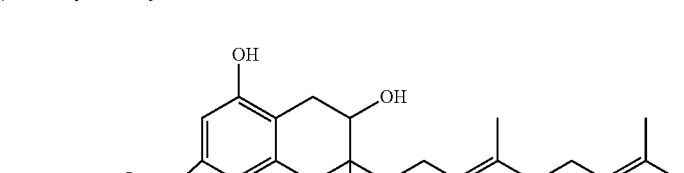 | D-ornithine |

TABLE 5-continued

| | Molecular weight | R = | Additive organic amino compound |
|---|---|---|---|
| SMTP-8 | 883.1 | (structure) | L-lysine |
| SMTP-8D | 883.1 | (structure) | D-lysine |
| SMTP-9 | 977.2 | (structure) | L-cystine |
| SMTP-29 | 839.1 | (structure) | DL-2,3-diaminopropionic acid |
| SMTP-31 | 925.2 | (structure) | DL-2,6-diaminopimelic acid |

The compounds shown in Table 5 can be preferably used as the compound represented by Formula (I) used in the disclosure.

Specific examples of the compound represented by Formula (I) include, in addition to the compound represented by Formula (II) or (III), the compounds shown in Tables 6 to 8 below.

TABLE 6
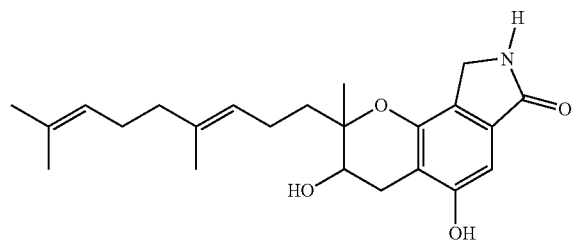
SMTP-0
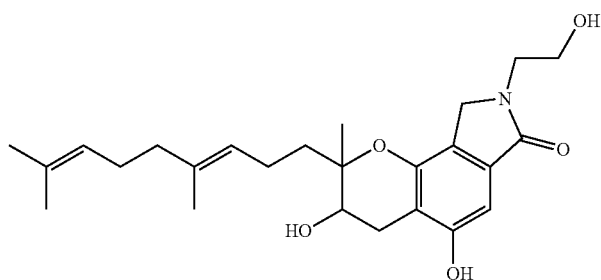
SMTP-1
| Compound No. | Molecular weight | Additive organic amino compound |
|---|---|---|
| SMTP-0 | 395.5 | Ammonium chloride |
| SMTP-1 | 429.6 | 2-aminoethanol |
TABLE 7
(Ib)
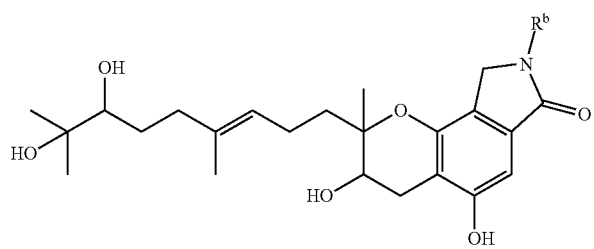
| Compound No. | $R^b$ |
|---|---|
| SMTP-0e | *—H |
| SMTP-2 | 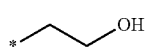 |
| SMTP-4e | 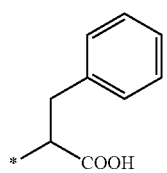 |
| SMTP-7e | 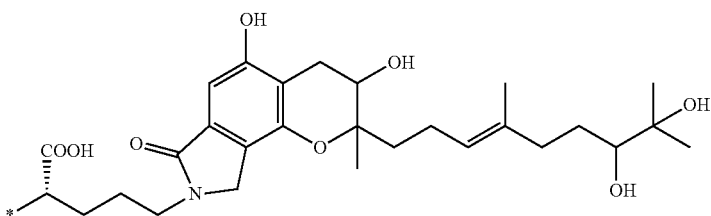 [SMILES: *[C@@H](CCCN1Cc2c(cc(O)c3c2OC(C)(CC/C=C(\C)CCC(O)C(C)(C)O)C(O)C3)C1=O)C(=O)O] |

TABLE 7-continued
| | |
|---|---|
| SMTP-21e | 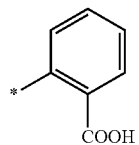 |
| SMTP-27e | 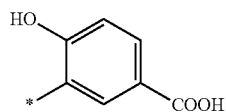 |
| SMTP-36e | 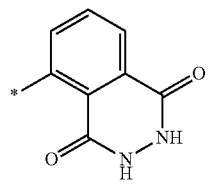 [SMILES: *c1cccc2c(=O)[nH][nH]c(=O)c12] |
| SMTP-43e | 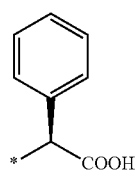 [SMILES: *[C@H](C(=O)O)c1ccccc1] |
(Ic)
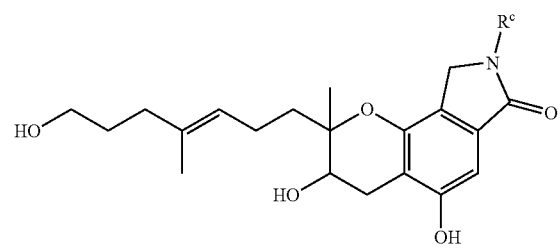
| Compound No. | $R^c$ |
|---|---|
| SMTP-0a | *—H |
| SMTP-4a | 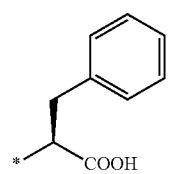 [SMILES: *[C@@H](Cc1ccccc1)C(=O)O] |
| SMTP-7a | 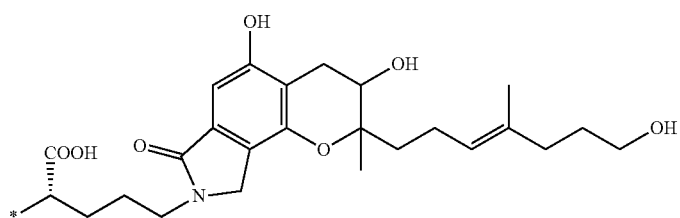 [SMILES: *[C@@H](CCCN1Cc2c(cc(O)c3c2OC(C)(CC/C=C(\C)CCCO)C(O)C3)C1=O)C(=O)O] |
| SMTP-21a | 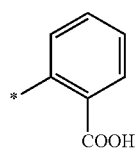 |

TABLE 7-continued
| | |
|---|---|
| SMTP-27a | 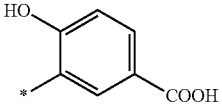 |
| SMTP-36a | 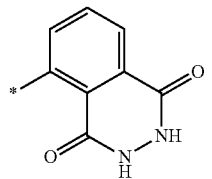 [SMILES: *c1cccc2c(=O)[nH][nH]c(=O)c12] |
| SMTP-43a | 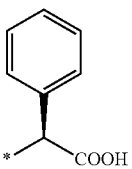 [SMILES: *[C@H](C(=O)O)c1ccccc1] |
TABLE 8
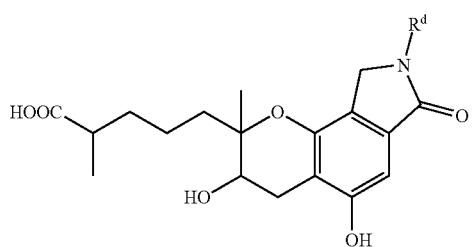
(Id)
| Compound No. | $R^d$ |
|---|---|
| SMTP-0b | *—H |
| SMTP-4b | 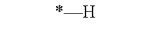 |
| SMTP-7b | 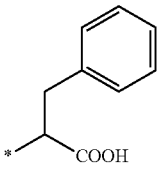 [SMILES: *C(Cc1ccccc1)C(=O)O] |
| SMTP-21b | 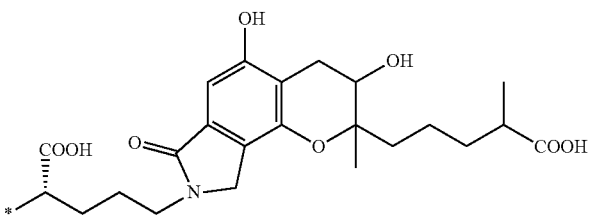 [SMILES: *[C@@H](CCCN1Cc2c(cc(O)c3c2OC(C)(CCCC(C)C(=O)O)C(O)C3)C1=O)C(=O)O] |
| SMTP-27b | 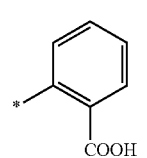 |

TABLE 8-continued
SMTP-36b 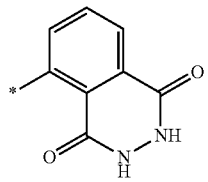 [SMILES: *c1cccc2c(=O)[nH][nH]c(=O)c12]
SMTP-43b 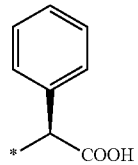
(Ie)
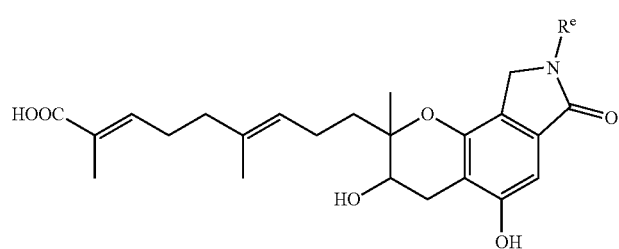
| Compound No. | $R^e$ |
|---|---|
| SMTP-0c | *—H |
| SMTP-4c | 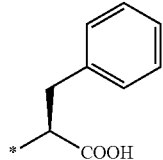 [SMILES: *[C@@H](Cc1ccccc1)C(=O)O] |
| SMTP-7c | 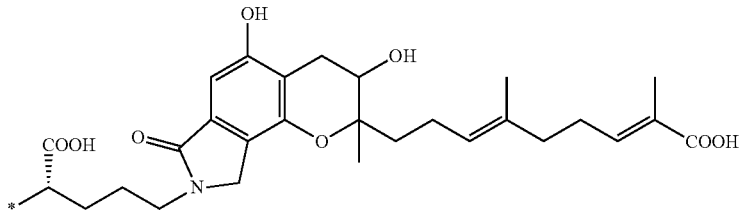 [SMILES: *[C@@H](CCCN1Cc2c(cc(O)c3c2OC(C)(CC/C=C(\C)CC/C=C(\C)C(=O)O)C(O)C3)C1=O)C(=O)O] |
| SMTP-21c |  |
| SMTP-27c | 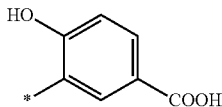 |
| SMTP-36c | 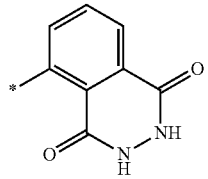 |

TABLE 8-continued

SMTP-43c

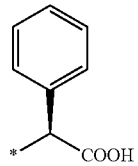 [SMILES: *[C@H](C(=O)O)c1ccccc1]

The compounds shown in Tables 6 to 8 can be preferably used as the compound represented by Formula (I) and contained in the drug . . .

Among the above-described compounds, the compound represented by Formula (I) preferably includes at least one selected from the group consisting of SMTP-0, SMTP-1, SMTP-4, SMTP-5D, SMTP-6, SMTP-7, SMTP-8, SMTP-11 to 14, SMTP-18 to 29, SMTP-36, SMTP-37, SMTP-42, SMTP-43, SMTP-43D, SMTP-44, SMTP-44D, SMTP-46, and SMTP-47, more preferably at least one selected from the group consisting of SMTP-7, SMTP-19, SMTP-22, SMTP-43, and SMTP-44D, and still more preferably SMTP-7.

A compound represented by Formula (I) used in the disclosure is contained in a drug in a liberated form, in a form of a pharmaceutically permissible salt or an ester, or in a form of a solvate. An inorganic acid, such as hydrochloric acid, hydrobromic acid, sulfuric acid, nitric acid, phosphoric acid, and an organic acid, such as citric acid, formic acid, fumaric acid, malic acid, acetic acid, succinic acid, tartaric acid, methanesulfonic acid, and p-toluenesulfonic acid are favorably used for forming a pharmaceutically permissible salt of a compound represented by Formula (I) used in the disclosure. Further, a compound containing an alkali metal, such as sodium, potassium, calcium, and magnesium, or an alkaline-earth metal, a basic amine, and a basic amino acid are also favorably used for forming a pharmaceutically permissible salt of a compound represented by Formula (I) used in the disclosure. Further, a C1 to C10 alcohol or a carboxylic acid, preferably methyl alcohol, ethyl alcohol, acetic acid, or propionic acid, is favorably used for forming a pharmaceutically permissible ester of a compound represented by Formula (I) used in the disclosure. Furthermore, water is also favorably used for forming a pharmaceutically permissible solvate of a compound represented by Formula (I) used in the disclosure.

The description of the specific examples of a compound represented by Formula (I) such as SMTP-7 includes these salt forms.

<Carrier and Additive>

There is no particular restriction on a kind of a carrier or a formulation additive used for preparing a drug according to the disclosure. A drug according to the disclosure is formulated using a compound represented by Formula (I) according to the disclosure, and a pharmaceutically permissible solid carrier (e.g., gelatin and lactose) or liquid carrier (e.g., water, a physiological saline solution, and a glucose aqueous solution).

<Dose>

Depending on a kind of a compound to be used as an active ingredient and the seriousness of renal disease, a drug according to the disclosure is administered preferably at 0.001 to 100 mg/kg as a single effective dose for an adult, and more preferably administered at 0.01 to 30 mg/kg. There is no particular restriction on the number of administrations, and any of one-time administration, multiple administrations, and a continuous administration is acceptable. The administration interval and administration duration can be selected by those skilled in the art according to clinical findings, image diagnostic findings, hematological findings, a comorbid disease, past history, etc.

In a case in which a drug according to the disclosure is used by multiple administrations, from the viewpoint of a sustainable contact of an affected part with the drug according to the disclosure, a mode with a continuous administration for 1 hour to 24 hours per day is preferable.

There is no particular restriction on an administration method, and various administration routes, such as intravenous administration, subcutaneous administration, intramuscular administration, and oral administration, can be selected. For example, at an acute phase of various diseases, an intravenous administration, more precisely an intravenous injection or a drip infusion can be used from the viewpoint of rapid and reliable administration of a desired dose to a patient. In that case, those skilled in the art may choose a rapid intravenous injection for 10% of a single dose, and a drip infusion over 30 minutes to 1 hour for 90% thereof.

<Use>

A drug according to the disclosure is a drug used for renal disease.

The drug according to the disclosure is preferably a drug used for treating or preventing renal disease.

In the disclosure, the term "treatment" means improvement or inhibition of a symptom, which includes inhibition of aggravation, and reduction or relaxation of a symptom.

In the disclosure, "prevention" means inhibition of onset, reduction of risk of onset, or delay of onset.

In the disclosure, use for renal disease means use when a symptom caused by renal disease is found and when it is predicted that a symptom caused by renal disease will appear.

The drug according to the disclosure is used for treating a symptom caused by renal disease, inhibiting the progression of the symptom, or relaxing the symptom. In this regard, the drug is used in combination depending on a usage period or a symptom in the usage period, which should not be limitedly interpreted.

Examples of a period in which a symptom caused by renal disease is found or a period in which a symptom caused by renal disease is predicted to appear include a period during or after a treatment of nephritis, renal ischemia, or other renal diseases. Alternatively, examples thereof include a period after administration of a drug such as cisplatin, a contrast medium, or any other drug having renal disease as a side effect, each of which is predicted to cause acute renal disease. In the period, the drug may be used prophylactically.

If a possibility of renal disease is found, the same may be used without limitation to the above-described periods.

The renal disease includes various kinds of renal damage and renal failure. A drug according to the disclosure can be used for both renal damage and renal failure, but is preferably used for renal failure.

Further, renal failure includes acute renal failure and chronic renal failure, and the drug according to the disclosure can be used for both acute renal failure and chronic renal failure.

The drug according to the disclosure is used for both chronic renal disease and acute renal disease.

Examples of the chronic renal disease include chronic renal ischemia, and renal disease caused by chronic nephritis.

Examples of the acute renal disease include renal diseases caused by acute renal ischemia and acute nephritis, and renal diseases caused by drug administration such as cisplatin nephropathy.

A drug according to the disclosure may be used without limitation to the use for humans. Examples of another subject for application include livestock such as cattle, horses, and sheep, and pets such as dogs, cats, and monkeys.

<Use in Combination with Other Drugs>

The drug according to the disclosure may be used singly, or in combination of at least one or more of other drugs used for renal disease.

The combined use of the drug according to the disclosure and another drug can be expected to enhance the therapeutic effect. In this case, the drug according to the disclosure and another drug can be used simultaneously or at different times.

In addition, a drug according to the disclosure may be used as a drug for preventing or treating renal disease by using the drug in combination with another drug having renal disease as a side effect.

Examples of the drug having renal disease as a side effect include cisplatin.

Examples according to the invention will be described below, but the invention is not limited thereto. Note that "%" is based on mass unless otherwise specified.

(Treatment or Prevention Method)

A treatment or prevention method according to the disclosure is a method of treating or preventing renal disease in a subject having or being at risk of developing renal disease, the method including administering the drug according to the disclosure to the subject at an effective amount for treating or preventing renal disease to the subject.

The treatment or prevention method according to the disclosure provides effects such as inhibition of aggravation of renal disease, reduction or relaxation of a symptom, inhibition of onset of renal disease, reduction of risk of onset, or delay of onset.

The dose, administration interval, administration duration, and administration method of a drug according to the disclosure in a treatment or prevention method according to the disclosure are the same as the drug according to the disclosure described above.

The treatment or prevention method according to the disclosure is applicable to both acute renal disease and chronic renal disease.

(Compound)

Another embodiment of the disclosure is the above-described compound represented by Formula (I) for treating or preventing renal disease.

The details of the dose regimen for treating or preventing renal disease and the like are the same as the above-described method for treating or preventing renal disease, and the preferred embodiments are also the same.

EXAMPLES

Examples according to the invention will be described below, but the invention is not limited thereto. Note that "%" is based on mass unless otherwise specified.

<Preparation of SMTP-7 and Edaravone>

SMTP-7 was produced according to a method described in JP-A No. 2004-224738 by purifying a culture medium obtained by adding L-ornithine as an additive organic amino compound to a culture medium of *Stachybotrys microspora*, strain IFO30018. To SMTP-7 obtained through purification and exsiccated, an aqueous solution of 0.3 N (0.3 mol/L) NaOH and a physiological saline solution (0.9% NaCl) were added to prepare a 50 mg/ml solution. Thereafter, the solution was adjusted using an aqueous solution of 0.3 N (0.3 mol/L) HCl and a physiological saline solution so that the concentration and pH of SMTP-7 were 10 mg/ml and weak alkaline, respectively. The resultant solution was subjected to filtration sterilization, divided into small fractions, and cryopreserved at −30° C. SMTP-7 was diluted with a physiological saline solution, if necessary, and the resultant was used.

SMTP-7 which had been cryopreserved was dissolved in a physiological saline solution at 1 mg/ml immediately before the test.

As edaravone (trade name: RADICUT, Mitsubishi Tanabe Pharma Corporation.), 1.5 mg/ml stock solution was used. The above-described medications were diluted with a physiological saline solution, if necessary.

Example 1: Test Using Chronic Renal Failure Animal Model

<Production of Chronic Renal Failure Animal Model>

A male ddY strain mouse (body weight: 30 g to 40 g) was used. Under anesthesia with isoflurane, the right flank of the mouse was incised, the renal arteries and veins were ligated, and then the right kidney was isolated. After suturing, acrinol was applied to the suture site as a disinfection treatment, and enrofloxacin was subcutaneously administered at 5 mg/kg as a preventive measure against infection, and acetaminophen was subcutaneously administered at 75 mg/kg as an analgesic treatment. After a recovery period of 3 to 4 weeks, the left abdomen of the mouse was incised, 100% acetic acid was applied to both sides of the kidney 10 times. This was defined as one course, and two courses were conducted at 5 minute intervals. After suturing, postoperative treatment was conducted in the same manner as in the removal of one of the kidneys. Considering the effect of surgery, a sham group to which acetic acid was not applied was provided.

<Administration of Drug>

4 weeks after the application of acetic acid, SMTP-7 was administered at a dose of 10 mg/kg or 30 mg/kg. The administration was carried out three times a week for 8 consecutive weeks by intraperitoneal administration. In addition, physiological saline was similarly administered to the sham group (without acetic acid application) and the Control group (with acetic acid application).

<Evaluation>

12 weeks after the application of acetic acid, urine was collected for 24 hours using a metabolic cage, and the urinary output was measured. During collecting urine, water was freely given. After urine collection, blood was collected from the descending aorta, the collected blood was centrifuged at 3000 rpm for 15 minutes, serum was separated, and BUN (urea nitrogen) and sCr (serum creatinine value) were measured. Further, protein and creatinine in the urine were also measured to calculate creatinine clearance (Ccr). BUN was measured using Urea B-test Wako (manufactured by Wako Pure Chemical Industries, Ltd.) and a QuantiChrom Urea Assay Kit (manufactured by Funakoshi Co., Ltd.), sCr was measured using Lab Assay Creatinine (manufactured by Wako Pure Chemical Industries, Ltd.), and urinary protein was measured using a BCA Protein assay kit (Thermo Fisher Scientific).

Renal function was evaluated by measuring BUN, sCr, urinary output, and urinary protein. In addition, urinary creatinine was measured to calculate creatinine clearance (Ccr). The measurement results are shown in Table 9.

TABLE 9

Effect of SMTP-7 on renal failure when applying acetic acid

| Treatment | N | BUN (mg/dL) | sCr (mg/dL) | Urinary output (ml/kg/day) | Urinary protein (mg/kg/day) | Ccr (mL/min/kg) |
|---|---|---|---|---|---|---|
| Sham | 13 | 35.9 ± 2.06 | 0.55 ± 0.03 | 67.7 ± 14.9 | 553 ± 87.4 | 2.29 ± 0.30 |
| Control | 11 | 80.3 ± :7.981 ** | 0.74 ± 0.02 * | 153 ± 37.2 * | 1118 ± 143 ** | 0.87 ± 0.14 ** |
| SMTP-7 10 mg/kg | 9 | 80.5 ± 13.3 | 0.71 ± 0.07 | 142 ± 31.7 | 968 ± 137 | 1.95 ± 0.23 |
| SMTP-7 30 mg/kg | 10 | 551 ± 1.57 # | 0.60 ± 0.05 # | 77.3 ± 18.5 | 527 ± 96.2 ## | 2.66 ± 0.37 ## |

* $P < 0.05$, ** $P < 0.01$: Statistically significant difference with respect to Control group
$P < 0.05$, ## $P < 0.01$: Statistically significant difference with respect to Sham group In Table 9, the experimental results are expressed in mean±standard error. With reference to statistically significant difference, an unpaired test between two groups (Student's t-test) was conducted for comparison between two groups, and one-way analysis of variance was conducted and then a Dunnett test was conducted for comparison among multiple groups. In all cases, a significance level of 5% or less ($P<0.05$) was regarded as significant difference.

[Evaluation Results of Blood Biochemical Parameter]

BUN and sCr in the Sham group were 35.9±2.06 mg/dL and 0.55±0.03 mg/dL, respectively. When acetic acid was applied, significant increase in the parameters (BUN: 80.3±7.981 mg/dL, sCr: 0.74±0.02 mg/dL) was recognized.

When SMTP-7 was administered, the above-described increase was inhibited in a dose-dependent manner, and there was significant difference in each parameter (BUN: 55.1±1.57 mg/dL, sCr: 0.60±0.05 mg/dL) between the 30 mg/kg administration group and the Control group.

[Evaluation Results of Urinary Parameters]

Urinary output and urinary protein in the Sham group were 67.7±14.9 ml/kg/day and 553±87.4 mg/kg/day, respectively. When acetic acid was applied, these parameters were significantly increased (urinary output: 153±37.2 ml/kg/day, urinary protein: 1118±143 mg/kg/day), and significant difference was recognized compared to the sham group. When SMTP-7 (30 mg/kg) was administered, the urinary output tended to decrease (77.3±18.5 ml/kg/day), but no significant difference was recognized compared to the Control group.

However, dose-dependent inhibition of the increase in urinary protein was recognized, and significant difference was recognized between the 30 mg/kg administration group (527±96.2 mg/kg/day) and the Control group. Further, when acetic acid was applied, significant decrease in Ccr was recognized compared to the Sham group (Sham: 2.29±0.30 ml/min/kg, Control: 0.87±0.14 ml/min/kg). SMTP-7 inhibited decrease of Ccr in a dose-dependent manner, and significant difference was recognized between the 30 mg/kg administration group (2.66±0.37 ml/min/kg) and the Control group.

<Effects of Edaravone>

The experiment and evaluation were carried out in the same manner as in the SMTP-7 (30 mg/kg) administration group, except that edaravone (30 mg/kg) was administered instead of SMTP-7 in the SMTP-7 (30 mg/kg) administration group. The measurement results are shown in Table 10.

TABLE 10

| Treatment | N | Urinary output (ml/kg/day) | Urinary protein (mg/kg/day) |
|---|---|---|---|
| Sham | 8 | 78.3 ± 20 | 542 ± 87.1 |
| Control | 8 | 208 ± 51.7 * | 974 ± 166 * |
| Edaravone 30 mg/kg | 10 | 90.5 ± 16.9 # | 553 ± 109 # |

* $P < 0.05$, ** $P < 0.01$: Statistically significant difference with respect to Sham group
$P < 0.05$, ## $P < 0.01$: Statistically significant difference with respect to Control group Example 2: Test Using Acute Renal Failure Animal Model <Production of Acute Renal Failure Animal Model>

A male ddY strain mouse (30 g) was used as an experimental animal. Under anesthesia with isoflurane, the right flank was incised about 2 cm to expose the kidney. After ligating the renal arteries and veins and the ureter, the right kidney was isolated.

A recovery period of 2 weeks was given, and then an acute renal failure mouse model was produced. Under anesthesia with isoflurane, the left abdomen was incised about 3 cm to expose the left kidney, and the fat around the renal arteries and veins was removed. The blood flow in the left renal arteries and veins was blocked using an atraumatic clip, and the kidney was left in ischemia for 45 minutes. The blood flow was then reperfused by removing the atraumatic clip, the kidney was returned to the abdominal cavity, and the flank was sutured. Mice similarly subjected to the steps other than the ischemia and reperfusion steps using the atraumatic clip were designated as a sham group (eight mice).

<Production of Acute Renal Failure Animal Model>

Eight acute renal failure mouse models were randomly allocated into a control group in which a vehicle (physiological saline solution) had been administered, an SMTP-7 administration group (0.01 mg/kg, 0.1 mg/kg, 1 mg/kg, 10 mg/kg), an SMTP-27 administration group (30 mg/kg), an SMTP-44D administration group (30 mg/kg), and an edaravone administration group (3 mg/kg). After 15 minutes of the initiation of ischemia, the vehicle, SMTP-7, SMTP-27, SMTP-44D, and edaravone were continuously administered to the femoral vein for 30 minutes.

24 hours after the ischemia and reperfusion processes, urine was collected for 24 hours using a metabolic cage, and the urinary output (UF; μL/min/kg) was measured. During collecting urine, only water was freely given. After urine collection, the body weight of each mouse was measured, and blood was collected from the abdominal aorta under anesthesia with isoflurane. After blood collection, the left kidney was isolated and the fat was removed in physiological saline. The kidney weight (KW; mg/g) was measured, and then the kidney was fixed in a 10% neutral buffered formalin solution for Hematoxylin Eosin (HE) staining.

<Measurement of Renal Function Parameter>

The collected blood was centrifuged at 800×g for 15 minutes at 25° C. to collect serum. Further, the urine collected using a metabolic cage was also used to evaluate renal function. In order to evaluate parameters in the serum, blood urea nitrogen (BUN; mg/dL) was measured using a QuantiChrom Urea Assay Kit (Funakoshi Co., Ltd.). Serum creatinine concentration (Scr; mg/dL) and urinary creatinine concentration (Ucr; mg/dL) were measured using LabAssay (trademark) Creatinine (manufactured by Wako Pure Chemical Industries, Ltd.), and creatinine clearance (Ccr; mL/min/kg) was calculated. The concentrations of sodium in the serum and urine were measured using Fuji Dry Chem 7000 (manufactured by FUJIFILM Corporation), and fractional excretion of sodium ($FE_{Na}$; %) was calculated. Urinary albumin concentration (Ualb; mg/hr/kg) was measured using Albwel M (manufactured by Cosmo Bio Co., Ltd.).

The measurement results are shown in Table 11.

recognized. Significant difference was recognized with a significance level of less than 5% (P<0.05).

[Changes in UF and Ualb after Administration of SMTP-7, SMTP-27, SMTP-44D, and Edaravone]

UF (88.9±11.9 μL/min/kg) in the control group was increased significantly compared to UF (35.7±4.8 μL/min/kg) in the sham group. When SMTP-7 was administered, dose dependent improvement of UF (0.01 mg/kg; 74.6±12.8 μL/min/kg, 0.1 mg/kg; 82.5±8.8 μL/min/kg, 1 mg/kg 62.3±13.4 μL/min/kg, 10 mg/kg; 46.8±9.5 μL/min/kg) was recognized, but there was no statistically significant difference recognized. UF in the SMTP-27 (30 mg/kg) administration group was 77.8±16.4 μL/min/kg, UF in the SMTP-44D (30 mg/kg) administration group was 103.2±33.47 L/min/kg, and there was no statistically significant difference recognized. Further, in the edaravone (3 mg/kg) administration group (55.3±12.1 μL/min/kg), significant improvement in UF was recognized.

Ualb (1.3±0.2 mg/hr/kg) in the control group was increased significantly compared to Ualb (0.3±0.1 mg/hr/kg) in the sham group. When SMTP-7 was administered, dose dependent improvement of Ualb (0.01 mg/kg; 1.8±0.3 mg/hr/kg, 0.1 mg/kg; 1.1±0.3 mg/hr/kg, 1 mg/kg; 0.7±0.2 mg/hr/kg, 10 mg/kg; 0.5±0.1 mg/hr/kg) was recognized. In the SMTP-7 (10 mg/kg) administration group, significant improvement in Ualb, compared to the control group, was recognized. Ualb in the SMTP-27 (30 mg/kg) administration group was 2.0±0.4 mg/hr/kg, Ualb in the SMTP-44D (30 mg/kg) administration group was 1.3±0.3 mg/hr/kg, and no significant improvement was recognized. In the edaravone (3 mg/kg) administration group, significant improvement in Ualb was not recognized (0.9±0.2 mg/hr/kg).

[Changes in KW after Administration of SMTP-7, SMTP-27, SMTP-44D, and Edaravone]

KW (13.9±0.6 mg/g) in the control group was increased significantly compared to KW (9.0±0.4 mg/g) in the sham group. When SMTP-7 was administered, dose dependent improvement of KW (0.01 mg/kg; 14.5±0.6 mg/g, 0.1 mg/kg; 13.6±1.0 mg/g, 1 mg/kg; 11.2±0.8 mg/g, 10 mg/kg; 11.1±0.4 mg/g) was recognized. In the SMTP-7 (10 mg/kg

TABLE 11

| | UF (mL/min · kg) | Ualb (mL/min/kg) | KW (mg/g) | BUN (mg/dL) | Scr (mg/dL) | Ccr (mL/min/kg) | $FE_{Na}$ (%) |
|---|---|---|---|---|---|---|---|
| sham | 35.7 ± 4.8 | 0.3 ± 0.1 | 9.0 ± 0.4 | 38.4 ± 2.7 | 3.0 ± 0.0 | 2.8 ± 0.2 | 0.9 ± 0.0 |
| control | 88.9 ± 11.9 ** | 1.3 ± 0.2 ** | 13.9 ± 0.6 ** | 192.2 ± 44.3 ** | 1.7 ± 0.4 ** | 1.2 ± 0.4 ** | 5.2 ± 2.1 ** |
| SMTP-7 (10 mg/kg) | 46.8 ± 9.5 | 0.5 ± 0.1 # | 11.1 ± 0.4 ## | 44.1 ± 2.9 ## | 0.4 ± 0.0 ## | 3.1 ± 0.2 ## | 0.7 ± 0.1 ## |
| SMTP-7 (1 mg/kg) | 62.3 ± 13.4 | 0.7 ± 0.2 | 11.2 ± 0.8 * ## | 66.0 ± 11.3 ## | 0.5 ± 0.1 ## | 2.3 ± 0.4 # | 1.0 ± 0.2 ## |
| SMTP-7 (0.1 mg/kg) | 82.5 ± 8.8 * | 1.1 ± 0.3 ** | 13.6 ± 1.0 ** | 125.8 ± 28.7 ** ## | 1.0 ± 0.3 * ## | 1.7 ± 0.4 * | 2.3 ± 1.0 ## |
| SMTP-7 (0.01 mg/kg) | 74.6 ± 12.8 | 1.8 ± 0.3 ** | 14.5 ± 0.6 ** | 108.8 ± 26.6 * ## | 0.9 ± 0.2 * ## | 1.6 ± 0.3 ** | 1.8 ± 0.8 ## |
| edaravone (3 mg/kg) | 55.3 ± 12.1 | 0.9 ± 0.2 | 13.4 ± 0.6 ** | 61.1 ± 5.9 ## | 0.5 ± 0.0 ## | 2.1 ± 0.2 | 1.0 ± 0.1 ## |
| SMTP-27 (30 mg/kg) | 77.8 ± 16.4 | 2.0 ± 0.4 ** # | 13.8 ± 0.7 ** | 59.7 ± 10.5 ## | 0.5 ± 0.0 ## | 2.5 ± 0.1 ## | 0.8 ± 0.1 ## |
| SMTP-44D (30 mg/kg) | 103.2 ± 33.7 * | 1.3 ± 0.3 ** | 12.3 ± 1.2 ** | 55.7 ± 14.2 ## | 0.6 ± 0.1 ## | 2.3 ± 0.4 # | 1.2 ± 0.1 ## |

*P < 0.05, **P < 0.01: Statistically significant difference with respect to Sham group
P < 0.05, ##P < 0.01: Statistically significant difference with respect to Control group In Table 11, the experimental results are expressed in mean±standard error in eight mice in each group. For comparison among multiple groups, firstly, one-way analysis of variance (ANOVA) was conducted, and then a Bonferroni test was conducted, if significant difference was and 1 mg/kg) administration groups, significant improvement in KW, compared to the control group, was recognized. KW in the SMTP-27 (30 mg/kg) administration group was 13.8=0.7 mg/g, KW in the SMTP-44D (30 mg/kg) administration group was 12.3±1.2 mg/g, and no significant improvement was recognized. Further, in the edaravone (3 mg/kg) administration group, significant improvement in KW was not recognized (13.4±0.6 mg/g).

[Changes in BUN, Scr, Ccr, and $FE_{Na}$ after Administration of SMTP-7, SMTP-27, SMTP-44D, or Edaravone]

BUN (192.2±44.3 mg/dL) in the control group was increased significantly compared to BUN (38.4±2.7 mg/dL) in the sham group. When SMTP-7 was administered, dose dependent improvement of BUN (0.01 mg/kg; 108.8±26.6 mg/dL, 0.1 mg/kg; 125.8±28.7 mg/dL, 1 mg/kg; 66.0±11.3 mg/dL, 10 mg/kg; 44.1±2.9 mg/dL) was recognized. In the SMTP-7 administration group at all doses, significant improvement in BUN, compared to the control group, was recognized. BUN in the SMTP-27 (30 mg/kg) administration group was 59.7±10.5 mg/dL, BUN in the SMTP-44D (30 mg/kg) administration group was 55.7±14.2 mg/dL, and significant improvement was recognized. In the edaravone (3 mg/kg) administration group, significant improvement in BUN was also recognized (61.1±5.9 mg/dL).

Scr (1.7±0.4 mg/dL) in the control group was increased significantly compared to Scr (0.3±0.0 mg/dL) in the sham group. When SMTP-7 was administered, dose dependent improvement of Scr (0.01 mg/kg; 0.9±0.2 mg/dL, 0.1 mg/kg; 1.0±0.3 mg/dL, 1 mg/kg; 0.5±0.1 mg/dL, 10 mg/kg; 0.4±0.0 mg/dL) was recognized. In the SMTP-7 administration group at all doses, significant improvement in Scr, compared to the control group, was recognized. Scr was 0.5±0.0 mg/dL in the SMTP-27 (30 mg/kg) administration group, Scr was 0.6±0.1 mg/dL in the SMTP-44D (30 mg/kg) administration group, and significant improvement was recognized. In the edaravone (3 mg/kg) administration group, significant improvement in Scr was also recognized (0.5=0.0 mg/dL).

Ccr (1.2±0.4 mL/min/kg) in the control group was increased significantly compared to Ccr (2.8±0.2 mL/min/kg) in the sham group. When SMTP-7 was administered, dose dependent improvement of Ccr (0.01 mg/kg; 1.6±0.3 mL/min/kg, 0.1 mg/kg; 1.7±0.4 mL/min/kg, 1 mg/kg; 2.3±0.4 mL/min/kg, 10 mg/kg; 3.1=0.2 mL/min/kg) was recognized. In the SMTP-7 (10 mg/kg and 1 mg/kg) administration groups, significant improvement in Ccr, compared to the control group, was recognized. Ccr in the SMTP-27 (30 mg/kg) administration group was 2.5±0.1 mL/min/kg, and Ccr in the SMTP-44D (30 mg/kg) administration group was 2.3±0.4 mL/min/kg, and significant improvement was recognized. In the edaravone (3 mg/kg) administration group, significant improvement in Ccr was not recognized (2.1±0.2 mL/min/kg).

$FE_{Na}$ (5.2±2.1%) in the control group was increased significantly compared to $FE_{Na}$ (0.9±0.0%) in the sham group. When SMTP-7 was administered, dose dependent improvement of $FE_{Na}$ (0.01 mg/kg; 1.8±0.8%, 0.1 mg/kg; 2.3±1.0%, 1 mg/kg; 1.0=0.2%, 10 mg/kg; 0.7±0.1%) was recognized. In the SMTP-7 administration group at all doses, significant improvement in $FE_{Na}$, compared to the control group, was recognized. $FE_{Na}$ in the SMTP-27 (30 mg/kg) administration group was 0.8±0.1%, and $FE_{Na}$ in the SMTP-44D (30 mg/kg) administration group was 1.2±0.1%, and significant improvement was recognized. In the edaravone (3 mg/kg) administration group, significant improvement in $FE_{Na}$ was also recognized (1.0±0.1%).

<Production of Pathological Tissue Specimen>

24 hours after the ischemia and reperfusion processes, urine was collected for 24 hours using a metabolic cage, measurement of body weight was conducted, and blood was collected. Thereafter, nephrectomy was conducted, and formalin-fixed kidney was permeated with paraffin using an automatic embedding device to produce a paraffin block. The paraffin block was sliced into 3 μm sections with a microtome, and placed on a slide glass. Then, the sections were stretched with a paraffin stretcher at 52° C., and sufficiently dried overnight in a paraffin melter at 37° C. After deparaffinization and washing with water, the sections were stained with a Mayer's hematoxylin staining solution for 1 minute and washed with running water for 15 minutes. Thereafter, the sections were stained with an eosin staining solution for 45 seconds, and dehydrated with 80% to 100% ethanol, followed by clearing with xylene and sealing with marinol. Each specimen was examined microscopically at a magnification of 50 using an optical microscope. With respect to tubular dilatation, tubular necrosis, and tubular casts in the cortex, outer zone of outer medulla, and inner zone of outer medulla, the percentage of lesions in each site was evaluated according to the following criteria. The evaluation results are shown in Table 12.

0 point: No lesion
1 point: minimal lesion change (less than 20%)
2 points: mild lesion change (about 25%)
3 points: moderate lesion change (25% to 50%)
4 points: severe lesion change (50% or more)

TABLE 12

| Tubular dilatation score | Cortex | | Outer zone of outer medulla | | Inner zone of outer medulla | |
|---|---|---|---|---|---|---|
| sham | 0.0 ± 0.0 | | 0.0 ± 0.0 | | 0.1 ± 0.1 | |
| control | 3.4 ± 0.2 | ** | 2.9 ± 0.4 | ** | 2.8 ± 0.3 | ** |
| SMTP-7 (10 mg/kg) | 2.0 ± 0.3 | ** ## | 1.4 ± 0.4 | ** ## | 1.0 ± 0.2 | * ## |
| edaravone (3 mg/kg) | 3.0 ± 0.5 | ** | 2.4 ± 0.5 | ** | 2.4 ± 0.5 | ** |

| Tubular necrosis score | Cortex | | Outer zone of outer medulla | | Inner zone of outer medulla | |
|---|---|---|---|---|---|---|
| sham | 0.3 ± 0.2 | | 0.0 ± 0.0 | | 0.0 ± 0.0 | |
| control | 1.0 ± 0.0 | ** | 1.8 ± 0.4 | ** | 1.0 ± 0.0 | ** |
| SMTP-7 (10 mg/kg) | 0.4 ± 0.2 | ## | 0.4 ± 0.2 | ## | 0.5 ± 0.2 | ** ## |
| edaravone (3 mg/kg) | 0.9 ± 0.1 | ** | 0.9 ± 0.1 | ** ## | 0.9 ± 0.1 | ** |

| Tubular cast score | Cortex | | Outer zone of outer medulla | | Inner zone of outer medulla | |
|---|---|---|---|---|---|---|
| sham | 0.0 ± 0.0 | | 0.0 ± 0.0 | | 0.1 ± 0.1 | |
| control | 1.0 ± 0.0 | ** | 1.8 ± 0.3 | ** | 2.6 ± 0.3 | ** |
| SMTP-7 (10 mg/kg) | 0.9 ± 0.1 | ** | 0.9 ± 0.1 | ** ## | 1.0 ± 0.2 | ** ## |
| edaravone (3 mg/kg) | 0.9 ± 0.1 | ** | 1.0 ± 0.2 | ** ## | 1.5 ± 0.4 | ** ## |

*P < 0.05, **P < 0.01: Statistically significant difference with respect to Sham group
P < 0.01: Statistically significant difference with respect to Control group In Table 12, the experimental results are expressed in mean±standard error in eight mice in each group. For comparison among multiple groups, firstly, one-way analysis of variance (ANOVA) was conducted, and then a Bonferroni test was conducted, if significant difference was recognized. Significant difference was recognized with a significance level of less than 5% ($P<0.05$).

[Histopathological Changes after Administration of SMTP-7 and Edaravone]

In the control group, lesion changes in tubular dilatation, tubular necrosis, and tubular casts in the renal cortex, outer zone of outer medulla, and inner zone of outer medulla showed significantly higher scores than those in the sham group. In the SMTP-7 (10 mg/kg) administration group, lesion changes other than the lesion change in tubular casts in the renal cortex were significantly improved. Here, in the edaravone (3 mg/kg) administration group, lesion changes were significantly improved only in tubular necrosis and tubular casts in the outer zone of outer medulla of the kidney and tubular casts in the inner zone of outer medulla.

Example 3: Test Using Acute Renal Disease (Cisplatin Nephropathy) Animal Model

<Production of Acute Renal Disease (Cisplatin Nephropathy) Animal Model>

A male ddY strain mouse (30 to 40 g) was used as an experimental animal. Under anesthesia with isoflurane, cisplatin (20 mg/kg) was injected into the femoral vein at a constant rate over 15 minutes to induce nephropathy. 3 days later, blood was collected from the descending vena cava, and after separating serum, blood urea nitrogen (BUN) and serum creatinine (sCr) were measured to evaluate renal function. Further, the kidney was isolated after perfusion, RNA was extracted, reverse transcription was conducted, real-time RT-PCR was conducted using the produced cDNA as a template, and the effect on TNF-α mRNA expression in renal tissues was also studied. A group to which physiological saline was administered instead of cisplatin was designated as the sham group.

<Administration of Drug>

In order to study the timing of administration, a drug (10 mg/kg) was injected into the femoral vein at a constant rate simultaneously with cisplatin, or 1 or 2 days later. In order to study dose relationship, a drug (0.1 mg/kg, 1 mg/kg, or 10 mg/kg) was injected to the femoral vein at a constant rate.

Further, in order to study the effect on TNF-α mRNA expression and histopathological study, a drug (10 mg/kg) was similarly administered 1 day after administration of cisplatin.

<Measurement of BUN and sCr>

The collected blood was centrifuged at 3000 rpm for 15 minutes, serum was separated, and BUN and sCr were measured. In the measurement, BUN was measured using Urea B-test Wako (manufactured by Wako Pure Chemical Industries, Ltd.) and a QuantiChrom Urea Assay Kit (manufactured by Funakoshi Co., Ltd.), and sCr was measured using Lab Assay Creatinine (manufactured by Wako Pure Chemical Industries, Ltd.). The measurement results are shown in Table 13.

<RNA Extraction and Reverse Transcription>

In order to study a relationship between the level of TNF-α m-RNA expression and the time course of BUN and sCr, after the above-described blood collection, blood was removed by perfusing a physiological saline solution through the heart, and then the right kidney was isolated. The isolated kidney was homogenized using TRIzol (registered trademark) Reagent (Ambion), chloroform was added, and the mixture was mixed with a vortex mixer. After centrifugation at 4° C. and 12,000×g for 15 minutes, the aqueous layer was separated, isopropanol was added, and the mixture was incubated at room temperature for 10 minutes. After centrifugation at 4° C. and 12,000×g for 10 minutes, the supernatant was discarded. The pellet was washed with 75% ethanol and centrifuged at 4° C. and 7,500×g for 5 minutes. The supernatant was discarded, and the pellet was naturally dried.

The pellet was dissolved in RNase-free water and subjected to reverse transcription reaction using a SuperScript (registered trademark) VIRO cDNA Synthesis Kit (Invitrogen) to produce cDNA.

<Real Time RT-PCR>

Real time RT-PCR was conducted using SYBR GreenER (registered trademark) qPCR Super Mix for ABI PRISM (Invitrogen) with the cDNA produced in a manner as described above as a template. According to the SYBR GreenER protocol, 12.5 µL of SYBR GreenER, 2.5 µL of a primer (0.5 µL of a forward primer, 0.5 µL of a reverse primer for B-Actin), and 2.5 µL of the template were mixed for each primer and diluted to 25 µL with sterile purified water. A series of reactions at 50° C. for 2 min, at 95° C. for 10 min, at 95° C. for 15 sec, and at 60° C. for 1 min was repeated 40 times using a Real time PCR detection system (ABI PRISM 7900). Quantification was conducted using a calibration curve method.

The primers used were TNF-α (QT00104006), B-Actin forward, and B-Actin reverse. The TNF-α primer used was purchased from QIAGEN. All of the following primers were custom made by Invitrogen.

β-Actin forward:
5'-CCTTCCTTCTTGGGTATGGAATC-3'

β-Actin reverse:
5'-TGCTAGGAGCCAGAGCAGTAATC-3'

TABLE 13

|  | N | Treatment | BUN (mg/dL) | sCr (mg/dL) |
|---|---|---|---|---|
| Coadministration | 7 | Sham | 27.5 ± 1.98 | 0.58 ± 0.04 |
|  | 7 | Control | 65.5 ± 3.83 ** | 0.82 ± 0.04 ** |
|  | 7 | SMTP-7 | 66.3 ± 9.23 | 0.81 ± 0.09 |
| Administration one day later (1 day) | 6 | Sham | 28.6 ± 1.42 | 0.41 ± 0.02 |
|  | 7 | Control | 86.2 ± 18.5 ** | 1.11 ± 0.05 ** |
|  | 6 | SMTP-7 | 44.5 ± 2.19 # | 0.80 ± 0.07 ## |
| Administration two days later (2 day) | 7 | Sham | 29.9 ± 1.36 | 0.50 ± 0.03 |
|  | 7 | Control | 78.8 ± 9.31 ** | 0.96 ± 0.13 ** |
|  | 7 | SMTP-7 | 74.2 ± 17.8 | 0.78 ± 0.18 |

** $P < 0.01$: Statistically significant difference with respect to Sham group
$P < 0.05$, ## $P < 0.01$: Statistically significant difference with respect to Control group

TABLE 14

| Treatment | N | BUN (mg/dL) | sCr (mg/dL) |
|---|---|---|---|
| Sham | 7 | 26.7 ± 1.90 | 0.51 ± 0.04 |
| Control | 8 | 82.6 ± 9.67 ** | 0.97 ± 0.13 ** |
| SMTP-7 0.1 mg/kg | 7 | 57.0 ± 5.47 # | 0.78 ± 0.08 |
| SMPT-7 1 mg/kg | 7 | 45.0 ± 6.28 ## | 0.65 ± 0.09 # |

TABLE 14-continued

| Treatment | N | BUN (mg/dL) | sCr (mg/dL) |
|---|---|---|---|
| SMPT-7 10 mg/kg | 7 | 32.1 ± 4.63 ## | 0.53 ± 0.03 ## |

\*\* P < 0.01: Statistically significant difference with respect to Sham group
# P < 0.05, ## P < 0.01: Statistically signifcant difference with respect to Control group

TABLE 15

| Treatment | N | BUN (mg/dL) | sCr (mg/dL) | TNF-α (TNF-α/β-actin) |
|---|---|---|---|---|
| Sham | 10 | 25.3 ± 0.85 | 0.34 ± 0.04 | 0.39 ± 0.08 |
| Control | 9 | 89.3 ± 12.5 \*\* | 1.08 ± 0.36 \* | 0.64 ± 0.09 \* |
| SMTP-7 10 mg/kg | 10 | 55.9 ± 5.20 ## | 0.41 ± 0.07 # | 0.43 ± 0.07 # |

\* P < 0.05, \*\* P < 0.01: Statistically significant difference with respect to Sham group
# P < 0.05, ## P < 0.01: Statistically significant difference with respect to Control group In Tables 13 to 15, the experimental results are expressed in mean±standard error. The RT-PCR results were corrected with the amount of B-Actin as an endogenous control gene. With reference to statistically significant difference, an unpaired test between two groups (Student's t-test) was conducted for comparison between two groups, and one-way analysis of variance was conducted and then a Dunnett test was conducted for comparison among multiple groups. Further, in the histopathological study, a Mann-Whitney U test was conducted, and in all cases, a significance level of 5% or less (P<0.05) was regarded as significant difference.

[Results of Study of Timing of Administration (Table 13)]

In the Sham group, BUN was 27.5 to 29.9 mg/dL and sCr was 0.41 to 0.58 mg/dL. When cisplatin was administered, significant increase in BUN and sCr was recognized, compared to the sham group (BUN: 65.5 to 86.2 mg/dL, sCr: 0.82 to 1.11 mg/dL), and onset of nephropathy was confirmed.

With respect to this increase, when 10 mg/kg of SMTP-7 was administered simultaneously with cisplatin (Coadministration), no inhibitory effect on BUN (Cont: 65.5±3.83 mg/dL, SMTP-7:66.3±9.23 mg/dL) and sCr (Control: 0.82±0.04 mg/dL, SMTP-7:0.81±0.09 mg/dL) was recognized. However, when SMTP-7 was administered 1 day later (1 day), the increase was significantly inhibited (BUN: Control: 86.2±18.5 mg/dL, SMTP-7:44.5±2.19 mg/dL. sCr: Control: 1.11±0.05 mg/dL, SMTP-7:0.80±0.07 mg/dL).

In this regard, when SMTP-7 was administered 2 days later (2 day), inhibitory tendency was recognized, but no significant difference, compared to the Control administration group (BUN: Control: 78.8±9.31 mg/dL, SMTP-7: 74.2±17.8 mg/dL). sCr: Control: 0.96±0.13 mg/dL, SMTP-7:0.78±0.18 mg/dL) was recognized. Based on these results, in the subsequent studies, 1 day after administration of cisplatin, SMTP-7 was administered.

[Results of Dose Relationship Study (Table 14)]

In the sham group, BUN was 26.6±1.90 mg/dL and sCr was 0.51±0.04 mg/dL. When cisplatin was administered, BUN was 82.6±9.67 mg/dL and sCr was 0.97=0.13 mg/dL, which were increased significantly compared to the sham group.

SMTP-7 showed a dose-dependent inhibitory effect on any increase. Significant difference was recognized between BUN in the 0.1 mg/kg administration group, the 1 mg/kg administration group, or the 10 mg/kg administration group (0.1 mg/kg: 57.0±5.47 mg/dL, 1 mg/kg: 45.0±6.28 mg/dL, 10 mg/kg: 32.1±4.63 mg/dL) and BUN in the Control group, and significant difference was recognized between sCr in the 1 mg/kg administration group or the 10 mg/kg administration group (0.1 mg/kg: 0.78=0.08 mg/dL, 1 mg/kg: 0.65±0.09 mg/dL, 10 mg/kg: 0.53±0.03 mg/dL) and sCr in the Control group.

[Results of Study of Effect on TNF-α mRNA Expression (Table 15)]

An effect on TNF-α mRNA expression in renal tissues was studied. When cisplatin was administered, significant increase was recognized both in BUN (Sham: 25.3±0.85 mg/dL, Control: 89.3±12.5 mg/dL) and in sCr (Sham: 0.34±0.04 mg/dL, Control: 1.08±0.36 mg/dL). This increase was significantly inhibited by SMTP-7.

TNF-α mRNA expression was measured by real-time RT-PCR under this condition. When cisplatin was administered, the expression was increased from 0.39±0.08 to 0.64±0.09, and significant difference between the Sham group and the Control group was recognized. SMTP-7 showed an inhibitory effect on this increase (0.43±0.07), and significant difference compared to the control group was recognized.

<Histopathological Study>10 mg/kg of SMTP-7 was administered 1 day after administration of cisplatin, and 3 days later, the kidney was isolated by the same method as in the evaluation of real time RT-PCR, and the histopathological study was conducted.

Formalin-fixed kidney was permeated with paraffin using an automatic embedding device to produce a paraffin block. The paraffin block was sliced into 3 μm sections with a microtome, and placed on a slide glass. Then, the sections were stretched with a paraffin stretcher at 52° C., and sufficiently dried overnight in a paraffin melter at 37° C. After deparaffinization and washing with water, the sections were stained with a Mayer's hematoxylin staining solution for 1 minute and washed with running water for 15 minutes. Thereafter, the sections were stained with an eosin staining solution for 45 seconds, and dehydrated with 80% to 100% ethanol, followed by clearing with xylene and sealing with marinol. Each specimen was examined microscopically at a magnification of 50 using an optical microscope. The degree of damage was examined microscopically at a magnification of 100 and 5 fields of view (1 field=2 mm, 5 fields=10 mm) and scored according to the following criteria.

Score 0: No significant change
Score 1: damage range 1 mm or less
Score 2: damage range 1 to 2 mm
Score 3: damage range 2 to 5 mm
Score 4: damage range 5 mm or more

TABLE 16

| Histopathological findings | Group N | Sham 7 | | | | | | Control 8 | | | | | | SMTP-7 7 | | | | | |
|---|---|---|---|---|---|---|---|---|---|---|---|---|---|---|---|---|---|---|---|
| | Score | 0 | 1 | 2 | 3 | 4 | Mean | 0 | 1 | 2 | 3 | 4 | Mean | 0 | 1 | 2 | 3 | 4 | Mean |
| Degeneration Necrosis | | 7/7 | | | | | 0.0 | | 1/8 | 1/8 | 5/8 | 1/8 | 2.8** | 2/7 | 2/7 | 1/7 | 1/7 | 1/7 | 1.6 |
| Tublar dilatation (Hyaline casts) | | 7/7 | | | | | 0.0 | 3/8 | 5/8 | | | | 0.6* | 6/7 | 1/7 | | | | 0.1 |
| Regenerated tubules | | 6/7 | 1/7 | | | | 0.1 | 6/8 | 1/8 | | | | 0.3 | 7/7 | | | | | 0.0 |

*$P < 0.05$, **$P < 0.01$: Statistically significant difference with respect to Sham group <Results of Histopathological Study (Table 16)>

When cisplatin was administered, marked degeneration of proximal tubules, necrosis, tublar diratation, and hyaline casts were recognized. However, clear histological changes in the glomerulus were not recognized. Here, histopathological changes in the proximal tubules were recognized in the SMTP-7 administration group, but the level was lower than that in the Control group and no significant difference was recognized.

Figure 2:
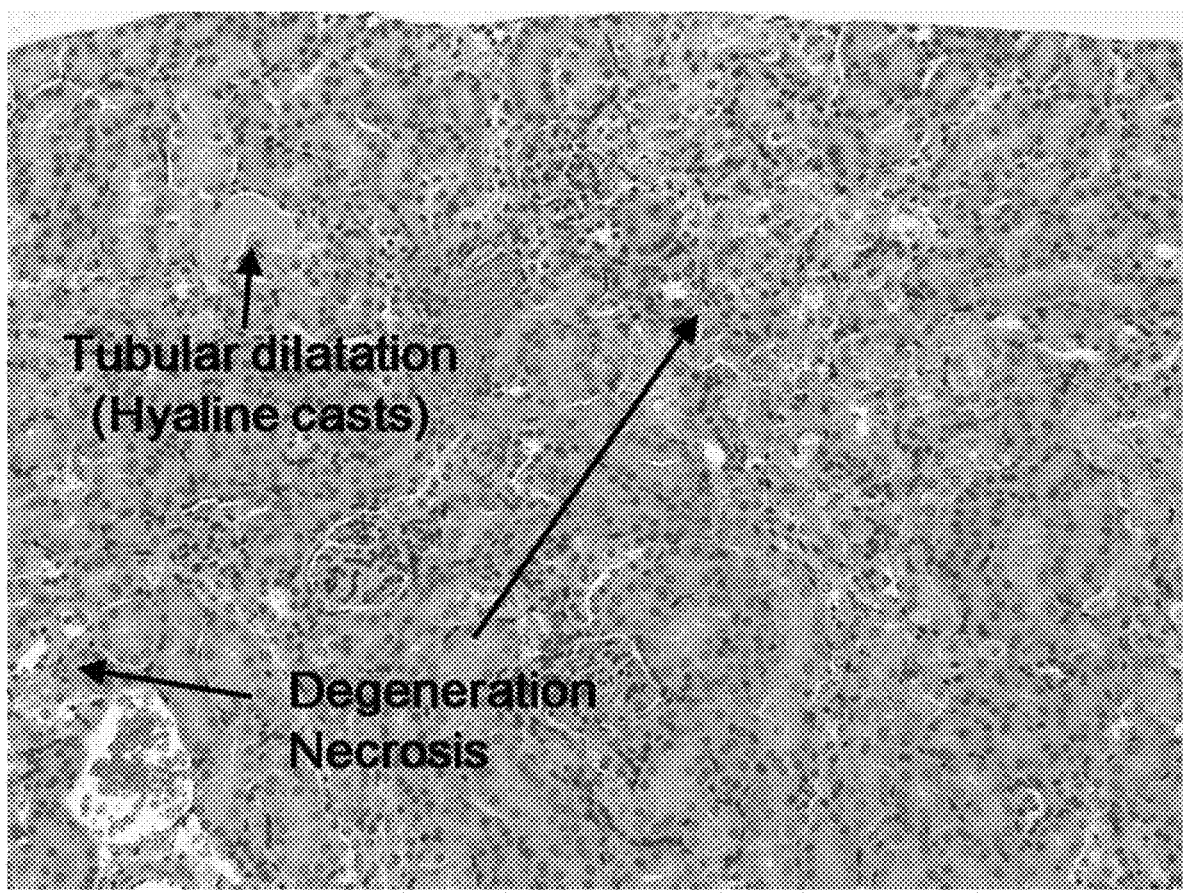
FIG. 2 is a view showing the result of HE staining in the Control group in a test using an acute renal disease (cisplatin nephropathy) animal model.
Figure 3:
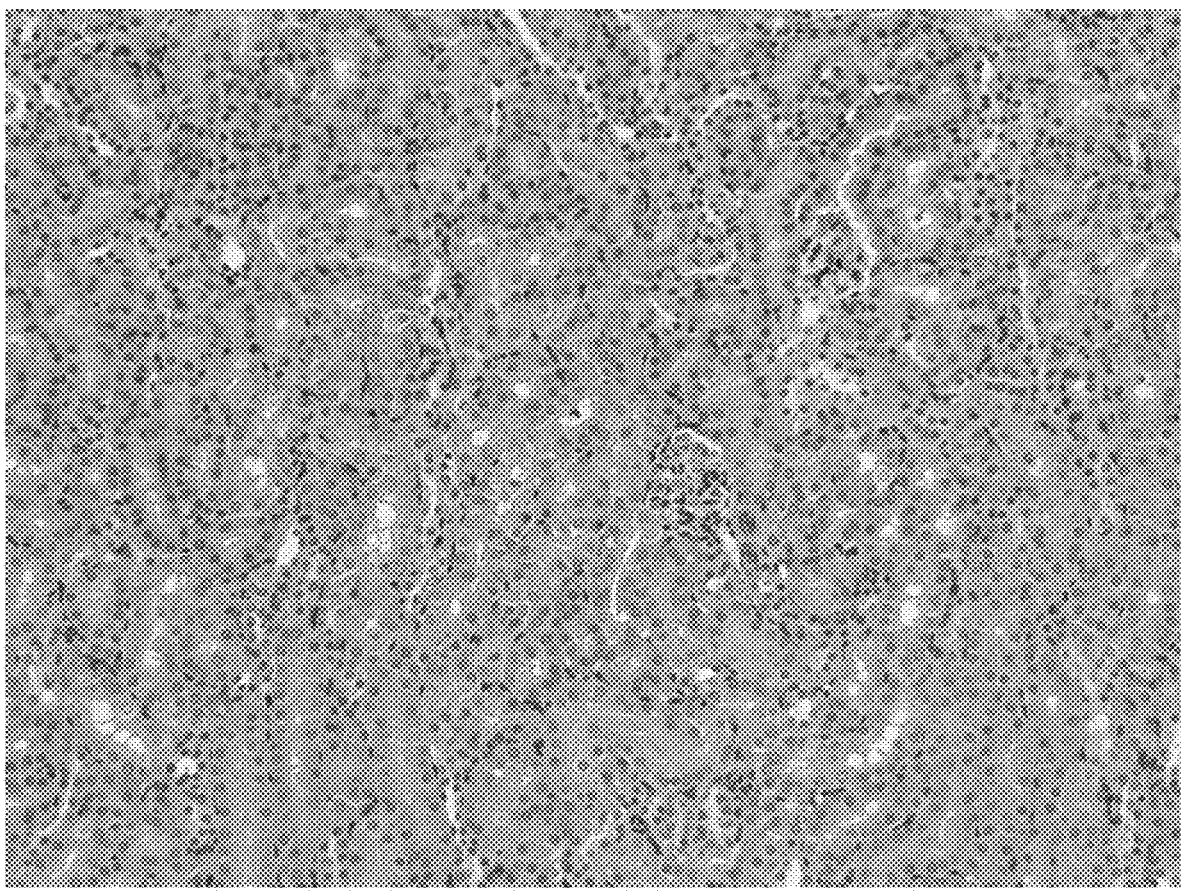
FIG. 3 is a view showing the result of HE staining in a group in which SMTP-7 was administered at 10 mg/kg one day after administration of cisplatin in a test using an acute renal disease (cisplatin nephropathy) animal model.

FIGS. 1 to 3 show one example of microscopic images based on histopathological study.

FIG. 1 shows the result of HE staining in the Sham group, FIG. 2 shows the result of HE staining in the Control group, and FIG. 3 shows the result of HE staining in the group in which SMTP-7 was administered at 10 mg/kg 1 day after administration of cisplatin.

From the above-described results, it can be seen that the drug according to the disclosure has therapeutic and preventive effects on chronic renal disease and acute renal disease.

The disclosure of Japanese Patent Application No. 2018-057055 filed on Mar. 23, 2018 is incorporated herein by reference in its entirety.

All publications, patent applications, and technical standards mentioned herein are incorporated herein by reference to the same extent as if such individual publication, patent application, or technical standard was specifically and individually incorporated by reference.

The invention claimed is:

1. A method of treating renal disease in a subject having renal disease, the method comprising administering the drug comprising a compound represented by the following Formula (I) or a salt thereof as an active ingredient to the subject at an effective amount for treating renal disease, wherein the renal disease is acute renal disease caused by acute renal ischemia:

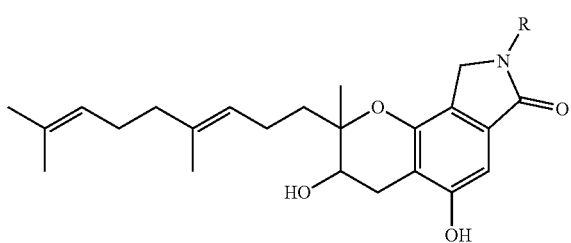

(I)

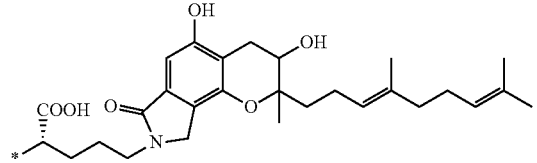

SMTP-7

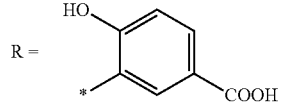

SMTP-27

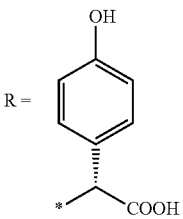

SMTP-44D wherein * represents a bonding site.

2. The method according to claim 1, wherein the effective amount is 0.01 to 30 mg/kg as a single effective dose for an adult.

3. The method according to claim 1, wherein the drug is administered with other medical agent simultaneously or/and at different times.

4. The method according to claim 1, wherein the drug is administered with an anticancer agent simultaneously or/and at different times.

5. The method according to claim 1, wherein the drug is administered with cisplatin simultaneously or/and at different times.

6. The method according to claim 1, wherein the compound is SMTP-7 or a salt thereof.

7. The method according to claim 1, wherein the compound is SMTP-7.

8. A method of treating renal disease in a subject having renal disease, the method comprising administering the drug comprising a compound represented by the following Formula (I) or a salt thereof as an active ingredient to the subject at an effective amount for treating renal disease, wherein the renal disease is acute renal disease caused by cisplatin nephropathy

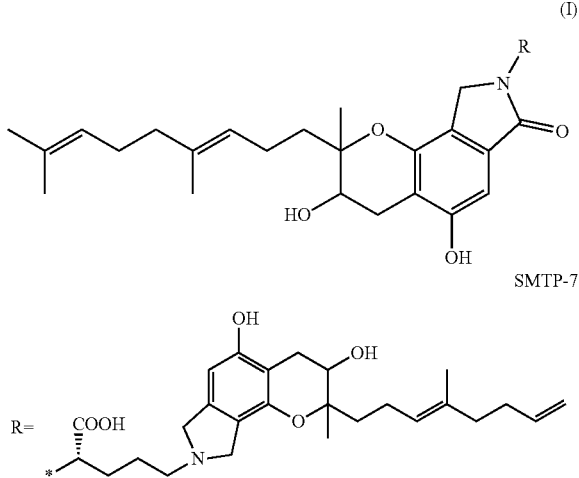

SMTP-7

R= 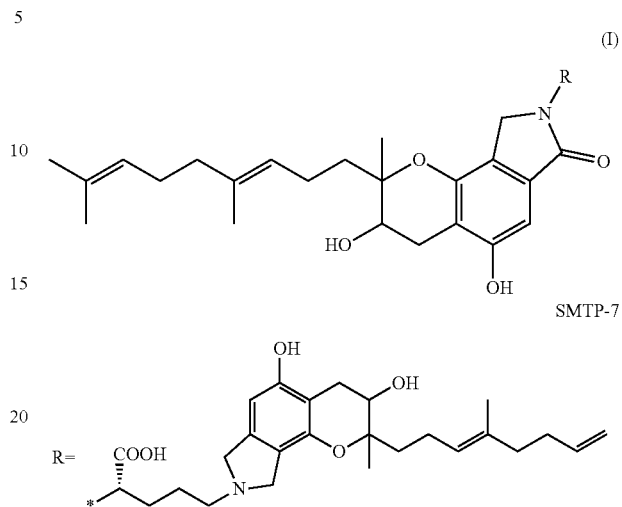

wherein * represents a bonding site.

9. The method according to claim 8, wherein the effective amount is 0.01 to 30 mg/kg as a single effective dose for an adult.

10. The method according to claim 8, wherein the drug is administered with other medical agent simultaneously or/and at different times.

11. The method according to claim 8, wherein the drug is administered with an anticancer agent simultaneously or/and at different times.

12. The method according to claim 8, wherein the drug is administered with cisplatin simultaneously or/and at different times.

13. The method according to claim 8, wherein the compound represented by the Formula (I) or the salt thereof is SMTP-7.

14. A method of treating renal disease in a subject having renal disease, the method comprising administering the drug comprising a compound represented by the following Formula (I) or a salt thereof as an active ingredient to the subject at an effective amount for treating renal disease, wherein the renal disease is chronic renal disease caused by cisplatin nephropathy wherein * represents a bonding site.

15. The method according to claim 14, wherein the effective amount is 0.01 to 30 mg/kg as a single effective dose for an adult.

16. The method according to claim 14, wherein the drug is administered with other medical agent simultaneously or/and at different times.

17. The method according to claim 14, wherein the drug is administered with an anticancer agent simultaneously or/and at different times.

18. The method according to claim 14, wherein the drug is administered with cisplatin simultaneously or/and at different times.

19. The method according to claim 14, wherein the compound represented by the Formula (I) or the salt thereof is SMTP-7.

* * * * *

UNITED STATES PATENT AND TRADEMARK OFFICE
CERTIFICATE OF CORRECTION

Page 1 of 1

PATENT NO. : 12,138,244 B2
APPLICATION NO. : 16/982523
DATED : November 12, 2024
INVENTOR(S) : Hashimoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 956 days.

Signed and Sealed this
Second Day of December, 2025

John A. Squires
*Director of the United States Patent and Trademark Office*